(12) United States Patent
Harlev et al.

(10) Patent No.: US 10,467,801 B2
(45) Date of Patent: *Nov. 5, 2019

(54) ANATOMICAL MODEL DISPLAYING

(71) Applicant: Affera, Inc., Watertown, MA (US)

(72) Inventors: Doron Harlev, Brookline, MA (US); Geoffrey Peter Wright, Boston, MA (US)

(73) Assignee: Affera, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/188,806

(22) Filed: Nov. 13, 2018

(65) Prior Publication Data
US 2019/0096122 A1   Mar. 28, 2019

Related U.S. Application Data

(63) Continuation of application No. 15/586,205, filed on May 3, 2017, now Pat. No. 10,163,252.

(Continued)

(51) Int. Cl.
*G06T 15/30* (2011.01)
*G06T 19/00* (2011.01)
(Continued)

(52) U.S. Cl.
CPC ............... *G06T 15/30* (2013.01); *A61B 1/04* (2013.01); *A61B 8/08* (2013.01); *A61B 8/0858* (2013.01);
(Continued)

(58) Field of Classification Search
CPC .......... A61B 8/0858; A61B 8/12; A61B 8/08; A61B 1/04; A61M 25/01; A61M 25/0108; G06T 5/006
See application file for complete search history.

(56) References Cited

U.S. PATENT DOCUMENTS 4,734,690 A   3/1988 Waller
5,276,785 A   1/1994 Mackinlay et al.
(Continued)

FOREIGN PATENT DOCUMENTS

WO    2005063125 A1    7/2005
WO    WO-2017192746    11/2017
WO    WO-2017192781    11/2017

OTHER PUBLICATIONS

Hilbert et al., Real-time magnetic resonance-guided ablation of typical right atrial flutter using a combination of active catheter tracking and passive catheter visualisation in man: initial results form a consecutive patient series, Eurospace 2016, vol. 18, Aug. 27, 2015, pp. 572-577.

(Continued)

*Primary Examiner* — Tapas Mazumder
(74) *Attorney, Agent, or Firm* — Perkins Coie LLP

(57) ABSTRACT

Systems and methods of automatically controlling, on a graphical user interface used by a physician, display views of an anatomic structure of a patient. Such systems and methods of automatically controlling display views of an anatomic structure of a patient can facilitate visualizing a position of a medical device relative to the anatomic structure during a medical procedure directed to the anatomic structure. In certain implementations, the systems and methods of the present disclosure provide automatic display views of a cardiac catheter relative to a three-dimensional model of a patient's heart cavity during a medical procedure such as cardiac ablation.

25 Claims, 6 Drawing Sheets

Related U.S. Application Data

(60) Provisional application No. 62/367,763, filed on Jul. 28, 2016, provisional application No. 62/357,600, filed on Jul. 1, 2016, provisional application No. 62/338,068, filed on May 18, 2016, provisional application No. 62/337,541, filed on May 17, 2016, provisional application No. 62/330,910, filed on May 3, 2016.

(51) Int. Cl.
*G06T 11/60* (2006.01)
*A61B 34/20* (2016.01)
*A61B 90/00* (2016.01)
*G06T 19/20* (2011.01)
*A61B 1/04* (2006.01)
*A61B 8/08* (2006.01)
*A61B 8/12* (2006.01)
*A61M 25/01* (2006.01)
*G06T 5/00* (2006.01)

(52) U.S. Cl.
CPC ............... *A61B 8/12* (2013.01); *A61B 34/20* (2016.02); *A61B 90/37* (2016.02); *A61M 25/01* (2013.01); *A61M 25/0108* (2013.01); *G06T 5/006* (2013.01); *G06T 11/60* (2013.01); *G06T 19/00* (2013.01); *G06T 19/20* (2013.01); *G06T 2200/24* (2013.01); *G06T 2210/41* (2013.01); *G06T 2219/004* (2013.01); *G06T 2219/028* (2013.01); *G06T 2219/2004* (2013.01); *G06T 2219/2012* (2013.01); *G06T 2219/2016* (2013.01)

(56) References Cited

U.S. PATENT DOCUMENTS

| | | |
|---|---|---|
| 5,391,199 A | 2/1995 | Ben-Haim |
| 5,433,198 A | 7/1995 | Desai |
| 5,687,737 A | 11/1997 | Branham et al. |
| 5,797,849 A | 8/1998 | Vesely et al. |
| 6,304,267 B1 | 10/2001 | Sata |
| 6,556,206 B1 | 4/2003 | Benson et al. |
| 6,664,986 B1 | 12/2003 | Kopelman et al. |
| 7,894,663 B2 | 2/2011 | Berg et al. |
| 8,014,561 B2 | 9/2011 | Farag et al. |
| 8,334,867 B1 | 12/2012 | Davidson |
| 8,784,413 B2 | 7/2014 | Govari et al. |
| 2003/0189567 A1 | 10/2003 | Baumberg |
| 2004/0249809 A1* | 12/2004 | Ramani ............... G06K 9/00201 |
| 2009/0163810 A1 | 6/2009 | Kanade et al. |
| 2009/0281418 A1* | 11/2009 | Ruijters .................... A61B 6/12 |
| | | 600/424 |
| 2010/0259542 A1 | 10/2010 | Visser et al. |
| 2011/0236868 A1* | 9/2011 | Bronstein .............. G09B 23/30 |
| | | 434/267 |
| 2012/0004540 A1* | 1/2012 | Liu .......................... A61B 5/06 |
| | | 600/424 |
| 2013/0241929 A1 | 9/2013 | Massaeawa et al. |
| 2013/0286012 A1* | 10/2013 | Medioni ................. G06T 17/00 |
| | | 345/420 |
| 2014/0328524 A1 | 11/2014 | Hu et al. |
| 2015/0042657 A1 | 2/2015 | Smith-Casem et al. |
| 2015/0324114 A1 | 11/2015 | Hurley et al. |
| 2016/0147308 A1* | 5/2016 | Gelman ................... G06F 3/01 |
| | | 345/156 |
| 2017/0065256 A1 | 3/2017 | Kim et al. |
| 2017/0265943 A1 | 9/2017 | Sela et al. |
| 2017/0319172 A1 | 11/2017 | Harlev et al. |
| 2017/0323473 A1 | 11/2017 | Wright et al. |

OTHER PUBLICATIONS

International Search Report and Written Opinion dated Jul. 25, 2017; International Patent Application No. PCT/US2017/030928; 12 pages.
ISA, "PCT Application No. PCTUS17/30877 International Search Report and Written Opinion dated Jul. 25, 2017" 11 pages.

* cited by examiner

ANATOMICAL MODEL DISPLAYING

CROSS-REFERENCE TO RELATED APPLICATIONS

This application is a continuation of U.S. patent application Ser. No. 15/586,205, filed May 3, 2017, which claims the benefit under 35 U.S.C. § 119(e) of U.S. Provisional Patent Application No. 62/330,910, filed May 3, 2016, U.S. Provisional Patent Application No. 62/337,541, filed May 17, 2016, U.S. Provisional Patent Application No. 62/338,068, filed May 18, 2016, U.S. Provisional Patent Application No. 62/357,600, filed Jul. 1, 2016, and U.S. Provisional Patent Application No. 62/367,763, filed Jul. 28, 2016, with the entire contents of each of these applications hereby incorporated herein by reference.

This application is also related to the commonly-owned U.S. patent application Ser. No. 15/586,022, filed May 3, 2018, and entitled "MEDICAL DEVICE VISUALIZATION," the entire contents of which are hereby incorporated herein by reference.

BACKGROUND

Three-dimensional models are sometimes used to assist in placement or use of devices when such placement or use is not easily observable or practical. For example, in medical procedures, three-dimensional models are used to assist in the placement and use of medical devices as part of diagnosis or treatment of patients. An example of a medical procedure carried out with the assistance of the three-dimensional model is the use of radio frequency ("RF") catheter ablation to form lesions that interrupt abnormal conduction to terminate certain arrhythmias in the heart.

SUMMARY

The present disclosure is directed to devices, systems and methods of automatically controlling, on a graphical user interface, display views of an anatomic structure of a patient to facilitate, for example, visualizing a position of a medical device relative to the anatomic structure during a medical procedure performed on the anatomic structure. For example, the devices, systems and methods of the present disclosure can be used to provide automatic display views, on a graphical user interface, of a cardiac catheter (e.g., an ablation catheter) relative to a three-dimensional anatomical model of a patient's heart cavity during a medical procedure such as, for example, cardiac ablation. As compared to manually controlling display views of a three-dimensional anatomical model during a medical procedure, it should be appreciated the automated visualization according to the devices, systems, and methods of the present disclosure can improve the efficiency of medical procedures and, additionally or alternatively, reduce the need for communication between a physician (in a sterile field) and a technician (outside of the sterile field) regarding orientation of the three-dimensional anatomical model on a graphical user interface used by the physician during the procedure.

According to one aspect, a method includes 1. A method comprising obtaining a three-dimensional model of a heart cavity of a patient, receiving a signal indicative of a location of a catheter in the heart cavity of the patient, determining at least one geometric feature of the three-dimensional model, determining a display view of the three-dimensional model of the heart cavity based at least in part on the location of the catheter in the heart cavity, on one or more previous locations of the catheter in the heart cavity, and on the geometric feature of the three-dimensional model, and displaying, on a graphical user interface, the display view of the three-dimensional model of the heart cavity.

In some implementations, receiving the signal indicative of the location of the catheter in the heart cavity can include receiving a signal indicative of contact between the catheter and the heart cavity. For example, the signal indicative of contact can be a signal indicative of force between the catheter and the heart cavity.

In certain implementations, determining the at least one geometric feature can include calculating, in the three-dimensional model, a surface-normal direction in an area of the heart cavity local to the location of the catheter.

In some implementations, determining the at least one geometric feature can include determining a thinnest direction of the three-dimensional model.

In certain implementations, determining the at least one geometric feature can be based on determining a bounding box with the smallest volume that contains the three-dimensional model. For example, determining the at least one geometric feature can include generating three scalar values representing a normalized length of the bounding box in the direction of each respective orthogonal vector of a coordinate system of the bounding box and, based on a comparison of the three scalar values to one another, selecting a direction corresponding to one of the orthogonal vectors.

In some implementations, the method can further include determining at least one visualization preference of the three-dimensional model, wherein determining the display view is further based at least in part on the at least one visualization preference. For example, the at least one visualization preference can include a preferred orientation of the three-dimensional model. Additionally, or alternatively, determining the at least one visualization preference is based at least in part on a received user input.

In certain implementations, determining the display view of the three-dimensional model can be based at least in part on the received location signal over a period of time. For example, the received signal indicative of location of the catheter can be a time-varying signal, receiving the signal indicative of the location of the catheter can include processing the time-varying signal, and determining the display view of the three-dimensional model can be based at least in part on the processed, received location signal. As a more specific example, processing the time-varying signal indicative of location of the catheter can include low-pass filtering the time-varying signal.

In some implementations, determining the display view can be further based at least in part on analysis of the shape of the three-dimensional model of the heart cavity of the patient.

In certain implementations, determining the display view can be further based at least in part on visualization preferences.

In some implementations, determining the display view can be further based at least in part on one or more previously displayed views.

In certain implementations, determining the display view can include adjusting a size of the three-dimensional model as projected onto a viewing window, and displaying the display view can include displaying a projection of the three-dimensional model onto the graphical user interface according to the adjusted size. For example, adjusting the size of the three-dimensional model projected onto the viewing window can be based on at least one of a size of the viewing window on an image plane, a relative position of the image plane to the three-dimensional model, and a relative position between the viewing window and a center of projection for the projection of the three-dimensional model. Additionally, or alternatively, at least one dimension of a viewing window can be maintained at a fixed multiple of a dimension of the projection of the three-dimensional model. For example, the dimension is a maximum width of the projection of the three-dimensional model in the image plane. Further, or in the alternative, determining the display view can include limiting pitch of the image plane relative to an axis defined by the three-dimensional model. Still further, or in the alternative, determining the display view can include limiting roll of the viewing window relative to an axis defined by the three-dimensional model. In certain instances, the method can further include, based at least in part on the received signal indicative of location of the catheter, determining a displacement speed of the catheter, and adjusting the size of the three-dimensional model projected onto the viewing window can be based at least in part on the determined displacement speed of the catheter.

In some implementations, displaying the display view of the three-dimensional model of the heart cavity can include displaying the determined view on a three-dimensional graphical user interface. For example, displaying the determined view on the three-dimensional graphical user interface can include displaying the determined view in an augmented reality environment. Additionally, or alternatively, displaying the determined view on the three-dimensional graphical user interface can include displaying the determined view in a virtual reality environment.

According to another aspect, a method includes obtaining a three-dimensional model of an anatomic structure of a patient, the three-dimensional model including a defined surface. receiving a signal indicative of a location of a catheter in the anatomic structure of the patient, based at least in part on the location of the catheter in the anatomic structure and on the defined surface, determining a display view of the three-dimensional model of the anatomic structure, and displaying, on a graphical user interface, the display view of the three-dimensional model of the anatomic structure.

In some implementations, the defined surface of the three-dimensional model can include a surface mesh of the three-dimensional model.

In certain implementations, the defined surface of the three-dimensional model can represent a blood-tissue boundary of the anatomic structure.

In some implementations, determining the display view of the three-dimensional model of the anatomic structure can be based at least in part on the location of the catheter relative to the defined surface of the three-dimensional model. For example, determining the display view of the three-dimensional model of the anatomic structure can be based at least in part on the location of the catheter relative to a local geometric feature of the defined surface of the three-dimensional model.

According to yet another aspect, a method of displaying a three-dimensional representation of a hollow anatomic structure of a patient includes obtaining a three-dimensional model of the hollow anatomic structure the patient, receiving a signal indicative of a location of a medical device in the hollow anatomic structure of the patient, determining a display view of the three-dimensional model of the hollow anatomic structure based at least in part on the location of the medical device in the hollow anatomic structure and on one or more previous locations of the medical device in the hollow anatomic structure, and displaying, on a graphical user interface, the display view of the three-dimensional model of the hollow anatomic structure.

In certain implementations, the method can further include determining at least one geometric feature of the three-dimensional model, wherein determining the display view can be further based at least in part on the at least one geometric feature of the three-dimensional model.

In some implementations, the method can further include determining at least one visualization preference of the three-dimensional model, and determining the display view can be further based at least in part on the at least one visualization preference.

According to still another aspect, a method of displaying a three-dimensional representation of a patient's heart cavity includes obtaining a three-dimensional model of the heart cavity of the patient, receiving a signal indicative of location of a catheter in the heart cavity of the patient, determining a trajectory of display views of the three-dimensional model of the heart cavity based at least in part on the location of the catheter in the heart cavity and on one or more previous locations of the catheter in the heart cavity, and displaying, on a graphical user interface, the display views of the three-dimensional model of the heart cavity according to the determined trajectory.

In some implementations, the method further includes analyzing the shape of the three-dimensional model, and determining the trajectory of the display views can be further based on the analyzed shape of the three-dimensional model. For example, analyzing the shape of the three-dimensional model can include analyzing a local portion of the three-dimensional model based on the location of the catheter. Additionally, or alternatively, analyzing the shape of the three-dimensional model can include analyzing a local feature of the three-dimensional model based on the one or more previous locations of the catheter. Additionally, or alternatively, analyzing the shape of the three-dimensional model can include analyzing one or more global features of the three-dimensional model.

In some implementations, the method can further include obtaining one or more visualization preference, and =determining the trajectory of the display views can be further based on the one or more visualization preference. For example, the one or more visualization preference can include a preferred orientation of the three-dimensional model.

In certain implementations, determining the trajectory of the display views can be further based on one or more previously displayed views.

According to still another aspect, a method of controlling a display of a three-dimensional model of an anatomic structure of a patient includes obtaining the three-dimensional model of the anatomic structure of the patient, receiving a signal indicative of a location of a medical device in the anatomic structure, based at least in part on the location of the medical device in the anatomic structure, selecting a display rule, from a plurality of rules, for specification of an orientation of the three-dimensional model and an image plane, based at least in part on the display rule, specifying i) the orientation of the three-dimensional model and ii) the image plane, and displaying, on a graphical user interface, at least a portion of a projection of the three-dimensional model, in the specified orientation, on the specified image plane.

In certain implementations, the display rule can be based at least in part on the location of the medical device relative to the anatomic structure. Additionally, or alternatively, the display rule can be further based at least in part on one or more previous locations of the medical device relative to the anatomic structure.

In some implementations, the plurality of rules can include a local rule and a global rule, the local rule can be based at least in part on the location of the medical device relative to the three-dimensional model, and the global rule can be based at least in part on the shape of the three-dimensional model. For example, selecting the display rule can include selecting the local rule, the global rule, or a combination thereof based on a comparison of the location of the medical device to a prohibited region at least partially defined by the three-dimensional model. The global rule can be selected if the location of the medical device is within a boundary of the prohibited region. Additionally, or alternatively, the local rule is selected if the location of the medical device is a predetermined distance beyond a boundary of the prohibited region. In certain instances, a combination of the local rule and the global rule can be selected if the location of the medical device is within a predetermined transition distance relative to the prohibited region. For example, a relative weighting of the local rule to the global rule can vary (e.g., substantially linearly) as a function of a distance from the location of the catheter to the prohibited region.

In certain implementations, the prohibited region can be at least partially defined by a center of mass of a volume of fluid represented by the three-dimensional model. Additionally, or alternatively, the prohibited region can be substantially symmetric about at least one plane containing the center of mass of the volume.

In some implementations, the prohibited region can be substantially symmetric about a superior-inferior axis.

In some implementations, the prohibited region can be a double-infinite right cone having an opening angle of greater than about 5 degrees and less than about 90 degrees.

In certain implementations, the local rule can include determining a local direction vector based on the location of the medical device. For example, the local direction vector can be based at least in part on direction vectors normal to a surface of the three-dimensional model in an area local to the location of the medical device. Additionally, or alternatively, based on selection of the local rule, the specified image plane can be a plane perpendicular to an axis defined by the local direction vector. Further, or instead, selecting the display rule can include limiting pitch of the image plane relative to a superior-inferior axis. Still further, or in the alternative, selecting the display rule can include limiting roll of a viewing window relative to a superior-inferior axis, and the viewing window is in the image plane.

In certain implementations, the specified image plane can be outside of a surface boundary of the three-dimensional model.

In some implementations, the specified image plane can be based in part on the direction of the local direction vector.

In certain implementations, specifying the orientation of the three-dimensional model can include specifying a reference axis of the three-dimensional model and aligning the reference axis with a superior-inferior axis defined by the three-dimensional model. For example, the method can further include receiving an input indicative of a predetermined preferred direction of the reference axis. For example, the predetermined preferred direction of the reference axis is a superior direction of the anatomic structure.

In some implementations, if the global rule is selected, specifying the orientation of the three-dimensional model and the image plane can include determining a thinnest direction of the three-dimensional model of the anatomic structure and specifying the image plane in a plane perpendicular to an axis defined by the thinnest direction. For example, the specified image plane is outside of a surface boundary of the three-dimensional model.

In certain implementations, displaying the projection of the three-dimensional model on the graphical user interface can include determining a zoom magnitude. For example, at least one dimension of a viewing window in the image plane can be maintained at a fixed multiple of a dimension of the three-dimensional model in the image plane. Additionally, or alternatively, the width of the viewing window can be maintained at a fixed multiple to a maximum dimension of the three-dimensional model in the image plane. In certain instances, the method can further include, based at least in part on the received signal indicative of location of the medical device, determining a displacement speed of the medical device, wherein determining the zoom magnitude can be based at least in part on the determined displacement speed of the medical device. For example, determining the zoom magnitude based at least in part on the determined displacement speed of the medical device can include increasing the zoom magnitude as the displacement speed of the medical device decreases.

According to another aspect, a method of controlling two-dimensional views of a three-dimensional anatomical model can include generating a three-dimensional model of an anatomic structure of a patient, displaying (e.g., on a graphical user interface) a projection of the three-dimensional model, the projection on a viewing window of an image plane, receiving a signal indicative of a location of a medical device in the anatomic structure, based at least in part on the received signal indicative of the location of the medical device, determining a displacement speed of the medical device in the anatomic structure, and adjusting a zoom magnitude based at least in part on the determined displacement speed of the medical device.

In some implementations, the method can further include displaying an indication of the zoom magnitude on the graphical user interface.

In some implementations, adjusting the zoom magnitude can include decreasing the size of the viewing window with decreasing displacement speed of the medical device.

In certain implementations, adjusting the zoom magnitude can include adjusting a field of view.

In some implementations, adjusting the zoom magnitude can include adjusting a distance between the image plane and a center of projection.

In certain implementations, adjusting the zoom magnitude can include moving the viewing window and the center of projection relative to the three-dimensional model.

According to still another aspect, a non-transitory, computer-readable storage medium has stored thereon computer executable instructions for causing one or more processors to obtain a three-dimensional model of a heart cavity of a patient, receive a signal indicative of a location of a catheter in the heart cavity of the patient, determine at least one geometric feature of the three-dimensional model, determine a display view of the three-dimensional model of the heart cavity based at least in part on the location of the catheter in the heart cavity, on one or more previous locations of the catheter in the heart cavity, and on the geometric feature of the three-dimensional model, and display, on a graphical user interface, the display view of the three-dimensional model of the heart cavity.

According to yet another aspect, a system includes a medical device and a medical device interface unit in communication with the medical device. The medical device interface unit includes a graphical user interface, one or more processors, and a non-transitory, computer-readable storage medium having sorted thereon computer executable instructions for causing one or more processors to obtain a three-dimensional model of a heart cavity of a patient, receive a signal indicative of a location of a catheter in the heart cavity of the patient, determine at least one geometric feature of the three-dimensional model, determine a display view of the three-dimensional model of the heart cavity based at least in part on the location of the catheter in the heart cavity, on one or more previous locations of the catheter in the heart cavity, and on the geometric feature of the three-dimensional model, and display, on a graphical user interface, the display view of the three-dimensional model of the heart cavity.

Implementations can include one or more of the following advantages.

In certain implementations, the display view of the three-dimensional model can be based at least in part on the received location of the catheter in the heart cavity and on one or more previously received locations of the catheter in the heart cavity. Determining the display view based on one or more previously received locations of the catheter can, for example, reduce the likelihood of abrupt and/or large transitions that can disorient or otherwise distract a physician who is relying on a representation of the three-dimensional model as part of a medical procedure. Additionally, or alternatively, determining the display view based on one or more previously received locations of the catheter can reduce, or even eliminate, shakiness that can otherwise appear in an automated representation of the three-dimensional model based on catheter location.

In some implementations, the display view of the three-dimensional model can be based at least in part on the received location of the catheter in an anatomic structure and on the defined surface of the three-dimensional model. Determining the display view based on the received location of the catheter and on the defined surface of the three-dimensional model can facilitate, for example, providing acceptable views of the three-dimensional model as the catheter moves through the anatomic structure. As a more specific example, determining the display view based on the received location of the catheter and on the defined surface of the three-dimensional model can provide more information than would be discernible from views of the three-dimensional model derived from catheter position alone, at least because the display view based on the received location of the catheter and on the defined surface of the three-dimensional model can facilitate viewing the catheter relative to a surface of the anatomic structure. It should be appreciated that automated generation of such views of the medical device relative to the surface can be particularly advantageous in medical procedures performed on the surface of the anatomic structure. That is, in general, providing a viewpoint of the three-dimensional model that accounts for both the location of the medical device and the surface of the anatomic structure can facilitate proper placement of the catheter, by a physician, along a desired area of the anatomic surface to be diagnosed and/or treated.

In some implementations, the display view (e.g., a viewing window defined in an image plane) of the three-dimensional model can be based at least in part on displacement speed of the catheter. It should be appreciated that such changes to the display view based on displacement speed of the catheter can facilitate providing intuitive changes to the representation of the three-dimensional model. Such intuitive changes can, for example, reduce the need for manual adjustment of the representation of the three-dimensional model during a medical procedure.

Other aspects, features, and advantages will be apparent from the description and drawings, and from the claims.

BRIEF DESCRIPTION OF THE DRAWINGS

Like reference symbols in the various drawings indicate like elements.

DETAILED DESCRIPTION

The present disclosure is generally directed to devices, systems, and methods of controlling, on a graphical user interface (e.g., used by a physician or other medical personnel), display views of an anatomic structure of a patient during a medical procedure being performed on the anatomic structure of the patient. For example, the devices, systems, and methods of the present disclosure can be used to visualize a position of a medical device during a medical procedure being performed on the anatomic structure. By way of non-limiting example and for the sake of clarity of explanation, the devices, systems, and methods of the present disclosure are described with respect to visualization of a cardiac catheter inserted into a heart cavity as part of a diagnostic and/or ablation treatment associated with the treatment of cardiac arrhythmia. However, it should be appreciated that, unless otherwise specified, the devices, systems, and methods of the present disclosure can be used for any of various different medical procedures, such as procedures performed on a hollow anatomic structure of a patient, in which direct visual access to the medical procedure is impractical and/or can be improved by the use of a model of the anatomic structure. For example, the devices, systems, and methods of the present disclosure can, additionally or alternatively, be used in interventional pulmonology, brain surgery, and/or sinus surgery (e.g., sinuplasty).

As used herein, the term "physician" should be considered to include any type of medical personnel who may be performing or assisting a medical procedure.

As used herein, the term "patient" should be considered to include any mammal, including a human, upon which a medical procedure is being performed.

Figure 1:
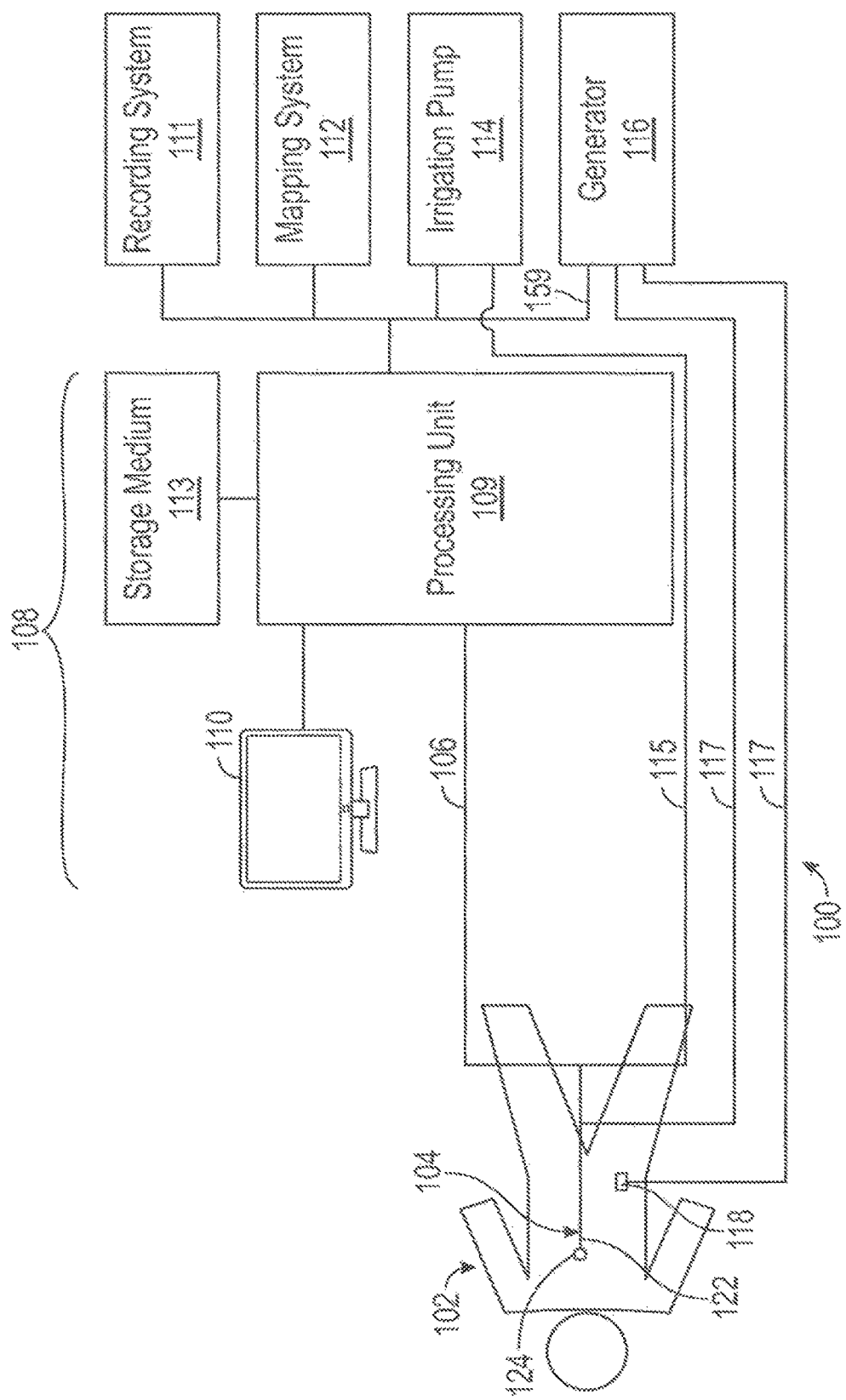
FIG. 1 is a schematic representation of a system during a medical treatment, the system including a catheter and a graphical user interface of a catheter interface unit.
Figure 2:
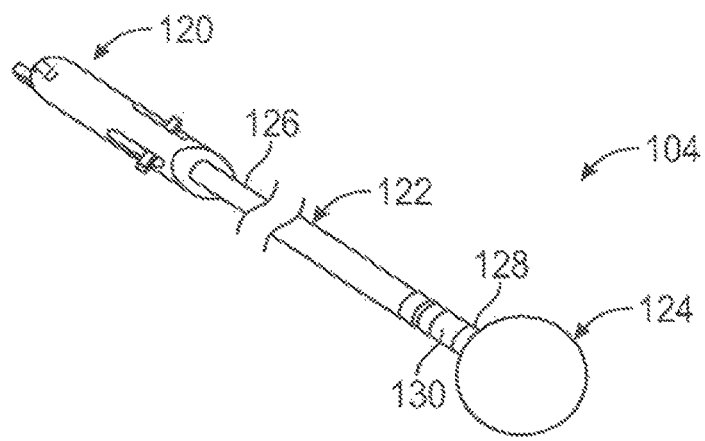
FIG. 2 is a perspective view of an ablation catheter of the ablation system of FIG. 1.
Figure 3:
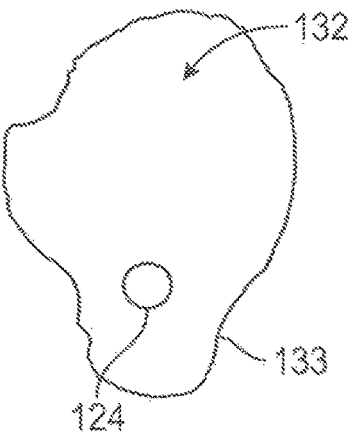
FIG. 3 is a schematic representation of a tip section of the ablation catheter of FIG. 2 in a heart cavity of a patient during an ablation treatment.

FIG. 1 is a schematic representation of a system 100 during a cardiac treatment (e.g., an ablation treatment) being performed on a patient 102. The system 100 can include a catheter 104 connected via an extension cable 106 to a catheter interface unit 108. The catheter interface unit 108 can include a processing unit 109 (e.g., one or more processors), a graphical user interface 110, and a storage medium 113. The graphical user interface 110 and the storage medium 113 can be in electrical communication (e.g., wired communication and/or wireless communication) with the processing unit 109.

One or more of a mapping system 112, a recording system 111, an irrigation pump 114, and a generator 116 can be connected to the catheter interface unit 108. The irrigation pump 114 is also removably and fluidly connected to the catheter 104 via fluid line 115. The generator 116 can be also connected via a wire 117 to a return electrode 118 attached to the skin of the patient 102.

The recording system 111 can be used throughout the procedure as well as before or after the treatment. The mapping system 112 can be used prior to or during the procedure to map the cardiac tissue of the patient 102 and, in the case of an ablation procedure, determine which region or regions of the cardiac tissue require ablation. As described in further detail below, the graphical user interface 110 can be used as part of diagnosis and/or treatment of the cardiac tissue of the patient 102 by, for example, displaying a three-dimensional model of a heart cavity of the patient 102 with the display automatically changing based on the location of the catheter 104 in the heart cavity of the patient 102. As compared to systems requiring manual control of a display of a three-dimensional representation of a heart cavity of the patient, displaying the three-dimensional representation on the graphical user interface 110 based on the location of the catheter 104 in the heart cavity of the patent 102 can reduce the complexity and time required to obtain useful views of the heart cavity.

Referring to FIGS. 1-4, the catheter 104 can include a handle 120, a catheter shaft 122, and tip section 124. The catheter shaft 122 can include a proximal portion 126 secured to the handle 120, and a distal portion 128 coupled to the tip section 124.

The tip section 124 can include any portion of the catheter 104 that directly or indirectly engages tissue for the purpose of treatment, diagnosis, or both and, therefore, can include all manner and type of contact and/or non-contact interaction with tissue known in the art. For example, the tip section 124 can include contact and/or non-contact interaction with tissue in the form of energy interaction (e.g., electrical energy, ultrasound energy, light energy, and any combinations thereof) and/or chemical interaction with tissue. Thus, for example, the tip section 124 can deliver energy (e.g., electrical energy) to tissue in the heart cavity as part of any number of treatment and/or diagnostic procedures. In certain implementations, such delivery of energy from the tip section 124 to the tissue can be through direct contact between the tip section 124 and the tissue. It should be appreciated that, while the tip section 124 is described as delivering energy to tissue through contact, such a description is provided here for the sake of clarity of explanation and that the systems and methods of the present disclosure can be implemented using any number and manner of designs of the catheter 104, including distal end portions of the catheter 104 that do not engage tissue and/or distal end portions of the catheter 104 that deliver other types of energy.

The catheter 104 can further include a magnetic position sensor 130 positioned along the distal portion 128 of the catheter shaft 122. It should be appreciated that the magnetic position sensor 130 can be any of various magnetic position sensors well known in the art and can be positioned at any point along the distal portion 128. The magnetic position sensor 130 can, for example, include one or more coils that detect signals emanating from magnetic field generators. As an example, one or more coils for determining position with five or six degrees of freedom can be used. The magnetic field detected by the magnetic position sensor 130 can be used to determine the position of the distal portion 128 of the catheter shaft 122 according to one or more methods commonly known in the art such as, for example, methods based on using the magnetic sensor to sense magnetic fields in the bed and using a look-up table to determine location of the magnetic position sensor 130. Accordingly, because the tip section 124 is coupled to the distal portion 128 of the catheter shaft 122 in a known, fixed relationship to the magnetic position sensor 130, the magnetic position sensor 130 can also provide the location of the tip section 124. While the location of the tip section 124 is described as being determined based on magnetic position sensing, other position sensing methods can additionally or alternatively be used. For example, the location of the tip section 124 can be additionally, or alternatively, based on impedance, ultrasound, and/or imaging (e.g., real time MRI or fluoroscopy).

A three-dimensional model 134 of a heart cavity 132 of the patient 102 can be built based on known positions of the tip section 124 of the catheter 104 in the heart cavity 132 (e.g., prior to application of the ablation treatment) and/or based on images of the heart cavity acquired prior to or during the procedure. The three-dimensional model 134 can be, for example, an anatomical model of the heart cavity 132 and displayed on the graphical user interface 110. In certain implementations, the graphical user interface 110 can be two-dimensional, and a two-dimensional representation of the three-dimensional model 134 can be projected onto the graphical user interface 110. It should be appreciated, however, that the graphical user interface 110 can additionally or alternatively include a three-dimensional display including, for example, an augmented reality environment and/or a virtual reality environment. Further, because the position of the tip section 124 is known, the position of the tip section 124 relative to a surface 133 of the heart cavity 132 can also be displayed on the graphical user interface 110.

In use, the tip section 124 of the catheter 104 can be inserted into a heart cavity 132 of the patient 102. Based on a signal received by the catheter interface unit 108 from the magnetic position sensor 130 (the received signal being used to determine the location of the tip section 124), the displayed view of the three-dimensional model 134 on the graphical user interface 110 can change automatically in response to movement of the tip section 124 within the heart cavity 132. For example, an orientation of the three-dimensional model 134 displayed on the graphical user interface 110 can be updated based on the location (e.g., changes in location) of the tip section 124 relative to the surface 133 of the heart cavity 132. Additionally, or alternatively, a size of the three-dimensional model 134 displayed on the graphical user interface 110 can be updated (e.g., based on a speed of location changes of the tip section 124). Because the display of the three-dimensional model 134 on the graphical user interface 110 can be responsive to the location of the tip section 124 in the heart cavity 132, the display of the three-dimensional model 134 can be automatically adjusted as the physician manipulates the handle 120 to deflect the distal portion 128 of the catheter shaft 122 to move the tip section 124 of the catheter 104 relative to desired diagnostic and/or treatment location in the heart cavity of the patient 102.

In an exemplary treatment, the tip section 124 can be placed into contact with a surface 133 of the heart cavity 132 and RF energy can be directed from the tip section 124 to the surface 133 of the heart cavity 132 to ablate tissue at some depth relative to the surface 133. Such ablations created by the tip section 124 along the surface 133 of the heart cavity can, for example, treat cardiac arrhythmia in patients with this condition. However, the effectiveness of ablations created using the tip section 124 along the surface 133 of the heart cavity 132 can be dependent upon location of the ablations. Accordingly, automatically adjusting display views of the three-dimensional model 134 of the heart cavity, according to the methods described herein, can be useful for the efficient and effective mapping of the heart and/or efficient and effective delivery of ablation treatment to treat cardiac arrhythmia.

The three-dimensional model 134 of the heart cavity 132 is stored on the storage medium 111, along with instructions executable by the processing unit 109 to display a display view 136 of the three-dimensional model 134 on the graphical user interface 110. The instructions stored on the storage medium 111 and executable by the processing unit 109 to display the display view of the three-dimensional model 134 can be, for example, an application built using Visualization Toolkit, an open-source 3D computer graphics toolkit, available at www.vtk.org.

Figure 5:
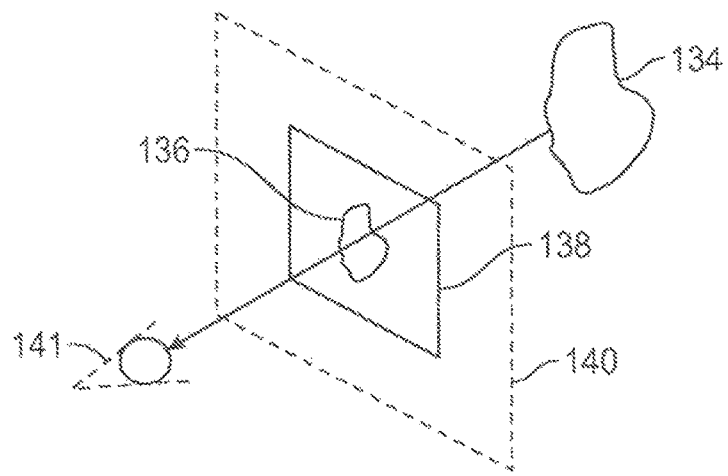
FIG. 5 is a schematic representation of the projection of the three-dimensional model of FIG. 4 onto a display view displayed on the graphical user interface of FIG. 1.

FIG. 5 is a schematic representation of the display view 136 of the three-dimensional model 134 projected onto the viewing window 138 displayed on the graphical user interface 110. It should be understood that the three-dimensional model 134 can be stored in a memory such as the storage medium 111 (FIG. 1). It should be further understood that projection of the three-dimensional model 134 can be carried out by the processing unit 109 (FIG. 1) executing computer-executable instructions stored on the storage medium 111 (FIG. 1).

Figure 4:
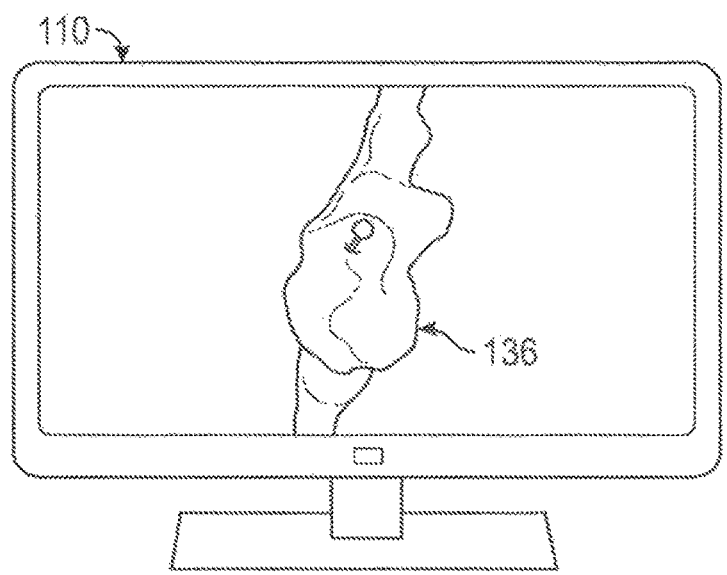
FIG. 4 is a schematic representation of the graphical user interface of FIG. 1 displaying a projection of a three-dimensional model of the patient's heart cavity during the ablation treatment of FIG. 3, the three-dimensional model stored on a storage medium of the catheter interface unit of FIG. 1.

Referring to FIGS. 4 and 5, in instances in which the graphical user interface 110 is a two-dimensional display, the three-dimensional model 134 can be projected to a viewing window 138 of an image plane 140 to form an image having a center of projection 141. The image plane 140 can correspond to a plane of the two-dimensional display of the graphical user interface 110, the viewing window 138 can correspond to a field of view of the two-dimensional display of the graphical user interface 110, and the center of projection 141 can correspond to the point of view of a user viewing the image on the graphical user interface 110. Accordingly, the image formed by projecting the display view 136 of the three-dimensional model 134 on the viewing window 138 can correspond to a specific orientation of the three-dimensional model 134 displayed on the graphical user interface 110.

One or more features (e.g., point-of-view and size) of the display view 136 forming the basis of the projection of the three-dimensional model 134 onto the viewing window 138 on the graphical user interface 110 can be a function of at least the position of the image plane 140 relative to the three-dimensional model 134, the size of the viewing window 136 on the image plane 140, and the distance between the viewing window 136 and the center of projection 141. For example, movement of the image plane 140 can result in corresponding movement of the display view. As the tip section 124 is moved within the heart cavity 132, the position (e.g., translation, orientation, or both) of the image plane 140 can change relative to the three-dimensional model 134 and/or the size of the viewing window 136 on the image plane 140 can change, resulting in corresponding changes in one or more of the point-of-view, location, and size of the display view 136 of the three-dimensional model 134 displayed on the graphical user interface 110. Additionally, or alternatively, as the tip section 124 is moved within the heart cavity 132, the position of the center of projection 141 can change, resulting in corresponding changes in one or more of the point-of-view, location, and size of the display view 136 of the three-dimensional model 134 displayed on the graphical user interface 110.

The computer executable instructions stored on the storage medium 111 (FIG. 1) can cause the processing unit 109 (FIG. 1) to display the three-dimensional model 134 on the display view 136 on the graphical user interface 110 according to one or more of the following exemplary methods. Unless otherwise indicated or made clear from the context, each of the following exemplary methods can be implemented using the system 100 (FIG. 1) and/or one or more components thereof.

Figure 6:
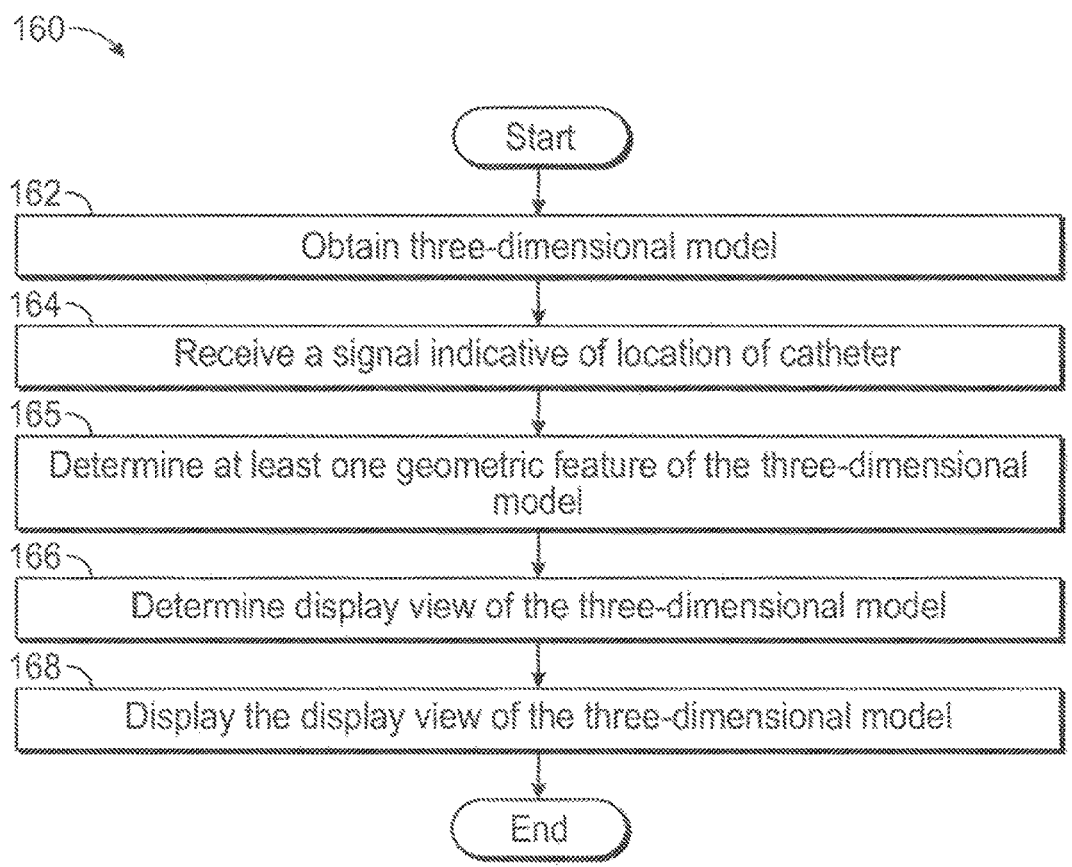
FIG. 6 is a flow chart of an exemplary process of displaying the three-dimensional model of FIG. 4 onto the graphical user interface of FIG. 1.

Referring now to FIG. 6, an exemplary method 160 of displaying a three-dimensional representation of a patient's heart cavity can include obtaining 162 a three-dimensional model of the heart cavity of the patient, receiving 164 a signal indicative of location of a catheter in the heart cavity of the patient, determining 165 at least one geometric feature of the three-dimensional model, determining 166 a display view of the three-dimensional model of the heart cavity, and 168 displaying (e.g., on a graphical user interface such as the graphical user interface 110 shown in FIG. 1) the display view of the three-dimensional model of the heart cavity. As described in greater detail below, determining 166 the display view of the three-dimensional model can be based on one or more of the received 164 location of the catheter, the at least one geometric feature of the three-dimensional model, and on one or more previously received locations of the catheter in the heart cavity. It should be appreciated that, although described below in the context of a heart cavity, the exemplary method 160 can be carried out to display a three-dimensional representation of other anatomic structures of a patient such as, for example, the brain, the lungs, the sinuses, and/or other hollow anatomic structures of the patient through which a catheter may be passed (e.g., for the purpose of diagnosis, treatment, or both).

In general, obtaining 162 the three-dimensional model of the heart cavity can include receiving and/or determining a three-dimensional model of the heart cavity prior to the procedure in which the display of the three-dimensional model is being controlled.

Obtaining 162 the three-dimensional model of the heart cavity can include, for example, receiving a plurality of locations of a catheter within the heart cavity and mapping the received visited locations of the catheter on a known coordinate system. In such implementations, a boundary of the visited locations can represent the blood-tissue boundary within the heart cavity. The plurality of received locations can be from the catheter being used as part of the exemplary method 160 and/or from another catheter (e.g., used as part of a previous procedure).

In certain implementations, obtaining 162 the three-dimensional model of the heart cavity can include receiving signals from a magnetic sensor disposed along a distal portion of a catheter (e.g., such as the magnetic sensor 130 described above) and building the three-dimensional model based on catheter locations determined from the received magnetic sensor signals. In addition, or in the alternative, the received plurality of locations of the catheter can be determined based on impedance of the catheter, ultrasound, imaging (e.g., fluoroscopy) and/or other known methods of determining catheter position.

In some implementations, obtaining 162 the three-dimensional model of the heart cavity can include receiving one or more images (e.g., computed tomography (CT) images, magnetic resonance imaging (MM) images, or both) of the heart cavity and registering the images to a coordinate system of the magnetic position sensor or other tracking sensor. These images can be acquired, for example, prior to the procedure. It should be appreciated, however, that these images can be additionally, or alternatively, acquired in real-time (e.g., using rotational angiography).

In general, receiving 164 the signal indicative of the location of the catheter in the heart cavity can include receiving a signal indicative of the location of the catheter according to any of the methods described herein. In certain instances, receiving 164 the signal indicative of location of the catheter in the heart cavity can include receiving a signal indicative of contact (e.g., indicative of force) between the catheter and the heart cavity. Further, as used herein, the location of the catheter refers to the location of a tip section of the catheter (e.g., the tip section 124 of the catheter 104 of FIG. 2). It should be understood, however, that the location of the catheter can include the location of any predetermined portion of the catheter in the heart cavity.

Receiving 164 the signal indicative of the location of the catheter in the heart cavity can include receiving the signal over a period of time. As a specific example, the signal indicative of the location of the catheter can be a time-varying signal. By determining 166 the display view based on the time-varying signal received over a period of time, the determined 166 display view can be based on one or more previously received locations of the catheter. By way of further explanation, one or more previously received locations, as used herein, should be understood to include one or more locations of the catheter received prior to a current time-step associated with the determined 166 display view. For example, the time-varying received 164 signal can be processed (e.g., by low-pass filtering the time-varying signal). The determined 166 display view can be based on the processed time-varying signal and, thus, can be based on one or more previously received locations of the catheter. Additionally, or alternatively, a display view can be based on the time-varying received 164 signal and the display view itself can be processed (e.g., by low-pass filtering the display view) such that the determined 166 display view can be based on one or more previous display views and is therefore based on one or more previously received locations of the catheter. In certain implementations, the parameters for processing the time-varying received 164 signal and/or the determined 166 display view can vary with the distance moved by the catheter.

Processing the time-varying signal can be useful, for example, for improved perception of the display view on the graphical user interface. For example, processing the time-varying signal of the received catheter location can smooth out changes in the display view corresponding to changes in location of the catheter. Through such smoothing, the resulting determined 166 display view can be more stable (e.g., less shaky), as compared to display views updated based on an unprocessed, time-varying signal. Accordingly, processing the time-varying signal can be useful for creating changes to the determined 166 display view at a rate that is both rapid enough to keep pace with changes in catheter position but slow enough to avoid large changes and/or many small rapid changes to the display view that are more likely to interfere with the physician's use of the three-dimensional model to position the catheter.

Determining 165 at least one geometric feature of the three-dimensional model includes any one or more of the various, different determinations described in further detail below. Thus, for example, determining 165 the at least one geometric feature of the three-dimensional model can include determining a surface-normal direction in an area of the heart cavity local to the received 164 location of the catheter. Additionally, or alternatively, determining 165 the at least one geometric feature of the three-dimensional model can include determining a thinnest direction of the three-dimensional model. Further, or instead, determining 165 the at least one geometric feature of the three-dimensional model can be based on determining a bounding box with the smallest volume that contains the three-dimensional model. Each of these determinations of the at least one geometric feature is set forth below with respect to the determination 166 of the display view.

In general, determining 166 the display view of the three-dimensional model can be based on one or more previously received locations of the catheter in the heart cavity. In certain implementations, determining 166 the display view can be based on one or more previously displayed views. For example, determining 166 the display view can include one or more rules (e.g., a hierarchy of rules), such as any of the rules described in further detail below, that constrain (e.g., reduce or prevent) certain transitions that are likely to be disruptive to a physician using the three-dimensional model to position the catheter. In certain implementations, determining 166 the display view can include a rule that prevents the determined 166 view from being rotated relative to a previously displayed view (e.g., an immediately previously displayed view) by greater than a predetermined threshold (e.g., greater than about 5 degrees) along a vertical axis of the three-dimensional model. Additionally, or alternatively, determining 166 the display view can include a rule that limits the rotation of the determined 166 view in one or more directions of rotation. For example, one or more of the roll and the pitch of the determined 166 view can be limited according to a predetermined rule.

In certain implementations, determination 166 of the display view can be based on the determination 165 of the at least one geometric feature of the three-dimensional model. Determining 166 the display view based on at least one geometric feature of the three-dimensional model can, for example, provide useful views during a medical procedure performed on tissue at the surface of an anatomic structure and, in addition or in the alternative, can account for variations in angles (axial or lateral) of engagement between the catheter and tissue during such medical procedures. An exemplary medical procedure of this type includes delivering energy to the surface of a heart cavity to create a lesion, during which it is generally desirable to view the catheter from the point of view of the surface facing the catheter, rather than from the point of view of the catheter toward the surface, and it is further, or alternatively, desirable to have a display view that automatically compensates for variations in angles of engagement between the catheter and tissue.

For example, as described in greater detail below, the geometric feature can be a local geometric feature of the three-dimensional model in the vicinity of the catheter, and the determined 166 display view can be oriented relative to this local geometric feature. As another example, also described in greater detail below, the geometric feature can be a global geometric feature (e.g., an overall shape of the three-dimensional model) of the heart cavity, and the determined 166 display view can be oriented relative to this global geometric feature. Further, the determined 166 display view can be determined according to the received 162 location of the catheter and a hierarchy of rules based at least in part on the local geometric feature and the global geometric feature.

Figure 7:
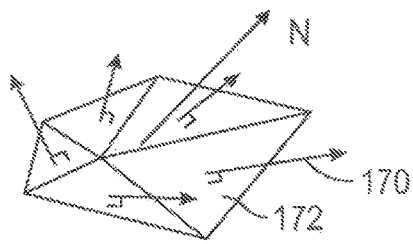
FIG. 7 is a schematic representation of a surface-normal direction in an area of a three-dimensional model local to a received location of a catheter.

Referring now to FIGS. 6 and 7, the at least one geometric feature can be a surface-normal direction N in an area of the three-dimensional model local to the received location of the catheter. For example, the surface-normal direction N can be a weighted sum of respective normal vectors 170 of surface elements 172 of the three-dimensional model within a threshold distance from the received location of the catheter. For example, the threshold distance can be less than about 1 cm radius from a point, on the surface mesh of the three-dimensional model, closest to the received location of the catheter. It should be appreciated that a lower bound of the threshold distance is the finite size including at least one normal vector.

In general, because the surface-normal direction N is a function of the received location of the catheter, the surface-normal direction N changes as the catheter moves relative to the surface of the heart cavity and, thus, relative to the surface represented in the three-dimensional model of the heart cavity. Further, because the surface-normal direction N is a function of local features in the vicinity of the received location of the catheter, determining 166 the display view based on the surface-normal direction N can facilitate automatically orienting the display view toward the most prominent features of the model in the vicinity of the received location of the catheter. For example, the determined 166 display view of the three-dimensional model can be oriented at a fixed angle (e.g., perpendicular or parallel) relative to the surface-normal direction N.

While the influence of local geometry on the surface-normal direction N can make the surface-normal direction N a useful parameter for determining 166 the display view, the surface normal direction N corresponding to certain local geometries may not be suitable for basing the determined 166 display view. For example, the surface-normal direction N of certain local geometries can extend in a direction that would produce a display view that violates one or more rules for the determined 166 display view. Accordingly, the surface-normal direction N can be used as at least one factor in determining whether the determined 166 display view is to be based on a local geometric feature or on a global geometric feature of the three-dimensional model. As one example, the determined 166 display view can be based on a global geometric feature of the three-dimensional model when a direction perpendicular to the surface-normal vector N is inappropriate (e.g., violates one or more predetermined display rules) for the determined 166 display view.

Figure 8:
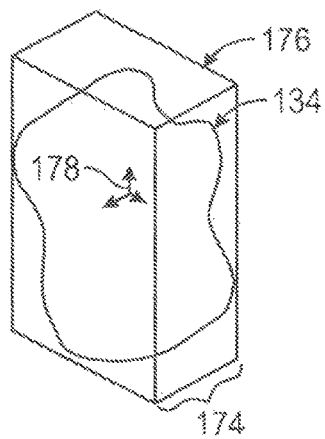
FIG. 8 is schematic representation of bounding box analysis of a three-dimensional model.

Referring now to FIGS. 6 and 8, a thinnest direction 174 of the three-dimensional model 134 is an example of a global geometric feature of the three-dimensional model that can be used to determine 166 the display view. For certain anatomic structures, such as certain heart cavities, the thinnest direction of the three-dimensional model is the direction that, in general, provides the least context with respect to the three-dimensional model. Accordingly, it can be advantageous to identify the thinnest direction and specify an image plane perpendicular to the thinnest direction such that the point of view of the determined 166 display view is parallel to the other two directions, which can provide more context (e.g., in the form of anatomic landmarks, etc.) to the physician.

In some implementations, a bounding box analysis can be used to determine the thinnest direction 174. For example, a bounding box 176 with the smallest volume that contains the three-dimensional model 134 can be determined. The bounding box 176 defines a three-dimensional coordinate system 178. The thinnest direction 174 of the bounding box 176 and, thus, the thinnest direction of the three-dimensional model 134, can be determined based on the length of the bounding box 176 in each dimension of the three-dimensional coordinate system 178. For example, the thinnest direction 174 of the bounding box 176 can be determined by generating three scalar values representing the normalized length of the bounding box in the direction of each respective orthogonal vector in the three-dimensional coordinate system 178, comparing the three scalar values to one another, and selecting a direction corresponding to one (e.g., the shortest) of the orthogonal vectors.

The determined 166 display view can be, for example, parallel to the thinnest direction 174. It should be appreciated, however, that the three-dimensional model 134 can have two sides along the thinnest direction 174. Accordingly, as described in greater detail below, the determined 166 display view can be parallel to the thinnest direction 174 and further determined according to a visualization preference of the three-dimensional model 134.

While the thinnest direction 174 has been described as one example of a global geometric feature, other types of geometric features can additionally or alternatively be used. For example, principal component analysis can be applied to the three-dimensional model 134. In general, such principal component analysis can facilitate identifying the orientation of the mass of the heart cavity and/or surface corresponding to the three-dimensional model 134. Thus, as compared to the bounding box approach to identifying a global geometric feature, principal component analysis can be less prone to being skewed by geometric features of the three-dimensional model 134 that, while extensive, do not correspond to the salient features of the three-dimensional model 134.

In implementations in which principal component analysis is used to identify a global geometric feature of the three-dimensional model 134, the determined 166 display view can be parallel to the direction representing the most mass of the heart cavity and/or surface. It should be appreciated that this orientation can be advantageous for providing the physician with the view of the three-dimensional model 134 that is most likely to provide useful contextual information.

In certain instances, the three-dimensional model 134 of the heart cavity may not have a substantially distinct global geometric feature (e.g., such as a global geometric feature determined using a bounding box analysis and/or a principal component analysis). As used herein, a substantially distinct global geometric feature can include a feature that exceeds other global geometric features by a threshold amount. Thus, for example, the three-dimensional model 134 can be substantially symmetrical (e.g., be sphere-like) such that, for example, bounding box analysis and/or principal component analysis produces three orthogonal vectors with approximately equal magnitudes. In such instances, the determined 166 display view can be oriented in a direction determined based on a local geometric feature of the three-dimensional model 134 such as, for example, based on the surface normal direction according to any of the methods described herein.

While determining 166 the display view has been described as being based on the received 164 location of the catheter and on one or more previously received locations of the catheter in the heart cavity, other implementations are additionally or alternatively possible. For example, determining 166 the display view can be based on the received location of the catheter in an anatomic structure and on a defined surface of the three-dimensional model. As a more specific example, determining 166 the display view of the three-dimensional model can be based on the received location of the catheter relative to the defined surface of the three-dimensional model (e.g., relative to a local geometric feature of the defined surface of the three-dimensional model such as any one or more of the local geometric features described herein).

The defined surface of the three-dimensional model can represent, for example, a blood-tissue boundary of an anatomic structure. Additionally, or alternatively, the defined surface can include a surface mesh of the three-dimensional model. The surface mesh can be determined according to any of various different methods that are well known in the art and include, for example, methods based on a boundary formed by locations visited by the catheter. The surface mesh can also, or instead, be determined from a volumetric dataset, such as a volumetric dataset from CT, MRI, or other imaging modalities. In such implementations, segmentation can be performed to identify the blood-tissue boundary, and a surface mesh can be fitted to that boundary.

While determining 166 the display view has been described as being based on at least one geometric feature of the three-dimensional model, it should be appreciated that determining 166 the display view can, additionally or alternatively, be based on a received indication of contact between the catheter and the tissue. The received indication of contact can be, for example, received from a force sensor disposed along the catheter tip and of any of various, different configurations well-known in the art.

The display view determined 166 based on the received indication of contact can be at a predetermined orientation relative to the received indication of contact. As an example, the display view can be opposite a force vector corresponding to the received indication of contact. As another non-exclusive example, the display view can be orthogonal to such a force vector.

The determined 166 display view can be, for example, based solely on the received indication of contact. Thus, in an exemplary implementation, the determined 166 display view can remain constant while the catheter is not in contact with tissue. Continuing with this exemplary implementation, upon detecting reengagement of the catheter with tissue (e.g., through a new received indication of contact), the determined 166 display view can be updated.

Additionally, or alternatively, the determined 166 display view can be based on a combination of the received indication of contact and the surface normal N local to the received 164 location of the catheter. For example, the determined 166 display view can be based on the received indication of contact when there is a received indication of contact and based on the surface normal N when there is no received indication of contact (e.g., when the catheter is not in contact with tissue). Further, or instead, the determined 166 display view based on the received indication of contact can override the display view based on the surface normal N based on predetermined criteria.

In certain implementations, comparing the display view determined 166 based on the received indication of contact to the display view determined 166 based on the surface normal N can provide useful insights with respect to the three-dimensional model, the received 164 location of the catheter, or both. For example, comparing the display view determined 166 based on the received indication of contact to the display view determined 166 based on the one or more local geometric features can provide an indication of how closely the three-dimensional model and the received 164 locations of the catheter correspond to their physical analogs. More specifically, the display view based on the received indication of contact can be substantially equivalent to the display view based on one or more local geometric feature when the three-dimensional model and the catheter positions match their physical analogs. Accordingly, it should be appreciated that differences in the display view based on the received indication of contact and the display view based on one or more local geometric feature can be useful, for example, for updating the three-dimensional model, the received 164 locations of the catheter, or combinations thereof.

While determining 166 the display view has been described as being based on anatomy (e.g., at least one geometric feature of the three-dimensional model) and/or based on a received indication of contact, it should be appreciated that, more generally, determining 166 the display view can be based on any one or more methods described herein for determining the point on the surface that is closest to the catheter.

As an example, the determined 166 display view can, additionally or alternatively, be based on a change in one or more electrical signals (e.g., change in impedance) associated with one or more respective sensors (e.g., electrodes) disposed along the catheter. In such implementations, a change in electrical signal can be an indication of contact. Continuing with this example, a change in one or more electrical signals associated with multiple different sensors can be indicative of contact as well as a direction of contact.

As another example, the determined 166 display view can be, additionally or alternatively, based on an imaging modality that can detect tissue. For example, one or more ultrasound transducers can be fitted onto the catheter to provide feedback regarding the point on the surface that is closest to the catheter. In such configurations, the point on the surface that is closest to the catheter can be visually or automatically discernible from the ultrasound image.

While determining 166 the display view can be based on a local geometric feature and/or a global geometric feature, determining 166 the display view can, additionally or alternatively, be based on at least one visualization preference for displaying the three-dimensional model. For example, a rule based hierarchy, such as a hierarchy based on a local geometric feature and a global geometric feature, can be further based on at least one visualization preference.

As used herein, the term "visualization preference" should be understood to be broadly defined to include a display rule that is not directly based on a local geometric feature or a global geometric feature. For example, a visualization preference can be predetermined (e.g., through a received user input) and/or determined based on previous display view of the three-dimensional model. In general, a visualization preference can reduce the likelihood that the determined 166 display view will be unacceptable and/or disruptive to a physician using the three-dimensional model to visualize a procedure that requires moving a catheter in the heart cavity.

Returning to the example of determining 166 the display view based on the thinnest direction 174 of the three-dimensional model 134, determining 166 the display view can further include a visualization preference in which, of the two possible sides of the three-dimensional model 134 to display, the side of the three-dimensional model 134 closest to a previously displayed view (e.g., immediately previously displayed view) of the three-dimensional model 134 is preferred. That is, unless this visualization preference is overridden by another rule in a hierarchy of rules, the display view will be oriented perpendicular to the thinnest direction 174 and along the side of the three-dimensional model 134 closest to the previously displayed view of the three-dimensional model 134. Such a display rule can, for example, reduce the likelihood that the determined 166 display view will result in an unacceptably large change in the display view that would be disruptive to the physician performing the procedure.

Determining 166 the display view can, further or instead, be at least partially based on a visualization preference including a preferred orientation of the three-dimensional model. For example, the preferred orientation can be an orientation similar to or the same as an orientation obtained using a visualization technique (e.g., x-ray). Such a preferred orientation can be useful, for example, for presenting an expected or familiar orientation of the three-dimensional model to the physician.

In certain implementations, determining 166 the display view can be at least partially based on a visualization preference including a received user input. For example, the physician can provide an input through an external device (e.g., a keyboard, a mouse, and/or a graphical user interface) to specify a visualization preference according to the physician's preference. In certain implementations, this input can be provided by the physician before the procedure. In some implementations, this input can be provided by the physician during the procedure.

Determining 166 the display view can further, or alternatively, be based at least in part on a relative orientation of a geometric feature (e.g., a global geometric feature) to the at least one visualization preference. As an example, the determined 166 display view can be based on snapping to a display view that incorporates a visualization preference. This can be understood, for example, by considering an implementation in which a display view based on a global geometric feature results in two possible display views (e.g., on opposite sides of the three-dimensional model) and the determined 166 display view includes selecting, from the two possible display views, the display view that is closest to the previously displayed display view. Thus, in certain instances, determining 166 the display view based at least in part on a relative orientation of a geometric feature to a visualization preference can advantageously reduce the likelihood of disorienting a physician using the three-dimensional model as part of a procedure.

Referring now to FIGS. 5 and 6, displaying 168 the display view can include displaying a two-dimensional display of the display view of the three-dimensional model. For example, the display view 136 can form a basis for projecting the three-dimensional model 134 onto a viewing window 138 defined in an image plane 140, which can correspond to a graphical user interface (e.g., the graphical user interface 110 in FIG. 4).

In certain implementations, determining 166 the display view can include adjusting a size of the three-dimensional model as projected onto the viewing window, and displaying 168 the display view can include displaying a projection of the three-dimensional model onto the graphical user interface according to the determined size. For example, adjusting the size of the three-dimensional model projected onto the viewing window can be based on a size of the viewing window on an image plane, a relative position of the image plane to the three-dimensional model, and a relative position between the viewing window and a center of projection for the three-dimensional model. In general, it should be appreciated that any one or more of these parameters can be varied to achieve a specific size of the projection of the three-dimensional model onto the viewing window. As used herein, the size of the projection of the three-dimensional model onto the viewing window is also referred to as a zoom magnitude.

For example, at least one dimension (e.g., the width, the height, or both) of the viewing window 138 can be a fixed percentage of a dimension (e.g., a maximum width, a maximum height, a maximum thickness) of the three-dimensional model projected onto the image plane 140. This percentage or multiple can be, in certain instances, about 20-30 percent larger than the projection of the determined display view of the three-dimensional model onto the viewing window. It should be readily appreciated, however, that other percentages or multiples are additionally, or alternatively, possible.

Implementations in which at least one dimension of the viewing window 138 is a fixed percentage larger than a dimension of the projection of the three-dimensional model can be useful, for example, for providing the physician with context for the displayed 168 display view of the three-dimensional model. That is, by displaying 168 the display view of the three-dimensional model such that a maximum dimension of the three-dimensional model is less than a dimension of the viewing window, one or more boundaries of the three-dimensional model can be displayed 168 on the graphical user interface. Such visible boundaries can, in certain instances, serve as visual cues to the physician regarding orientation of the displayed 168 three-dimensional model.

In some implementations, displaying 168 the display view of the three-dimensional model can be based on a displacement speed of the catheter. It should be appreciated that the displacement speed of the catheter can be determined, for example, based on changes in received location of the catheter as a function of time. Given that the displacement speed can be a time-varying signal, it should be further appreciated that any of the methods described herein as being based on displacement speed can include filtering (e.g., low-pass filtering) the displacement speed.

In general, displaying 168 the display view of the three-dimensional model can include changing the size of the three-dimensional model on the viewing window, and, thus, on the graphical user interface, as the displacement speed of the catheter changes. In some implementations, displaying 168 the display view can include changing the size of the projection of the three-dimensional model onto the viewing window in inverse relationship to the displacement speed of the catheter. For example, in instances in which the displacement speed of the catheter is relatively high, the size of the three-dimensional model on the viewing plane can be made to be relatively small such that rapid changes can be made to the display 168 of the three-dimensional model in response to rapid changes in the displacement of the catheter. Continuing with this example, in instances in which the displacement of the catheter is relatively low and thus updates to the displayed 168 view are also relatively slow, the size of the three-dimensional model on the viewing plane can be relatively large. This can be useful, for example, for facilitating observation of a specific area of the three-dimensional model by the physician, who may be moving the catheter slowly to observe an area of interest in the three-dimensional model 134.

Additionally, or alternatively, displaying 168 the zoom magnitude associated with the display view can be based on the received 164 catheter location including an indication of contact. That is, upon receiving an indication of contact, the zoom magnitude can be increased to provide a physician with a more detailed view of the area of the contact. In certain instances, the indication of contact can include an indication of force, and the zoom magnitude can be increased or decreased based on the indication of force. As an example, the zoom magnitude can be increased in response to the indication of force (e.g., with zoom magnitude increasing with increasing force).

It should be appreciated that while displaying 168 the determined 166 display view of the three-dimensional model has been described with respect to a two-dimensional display, the methods described herein are additionally, or alternatively, applicable to other types of displays. For example, all manner and methods of displaying 168 the determined 166 display view of the three-dimensional model to a three-dimensional graphical user interface are within the scope of the present disclosure. Examples of such three-dimensional displays to which the determined 166 display view of the three-dimensional model can be displayed 168 can include one or more of an augmented reality environment and a virtual reality environment.

Figure 9:
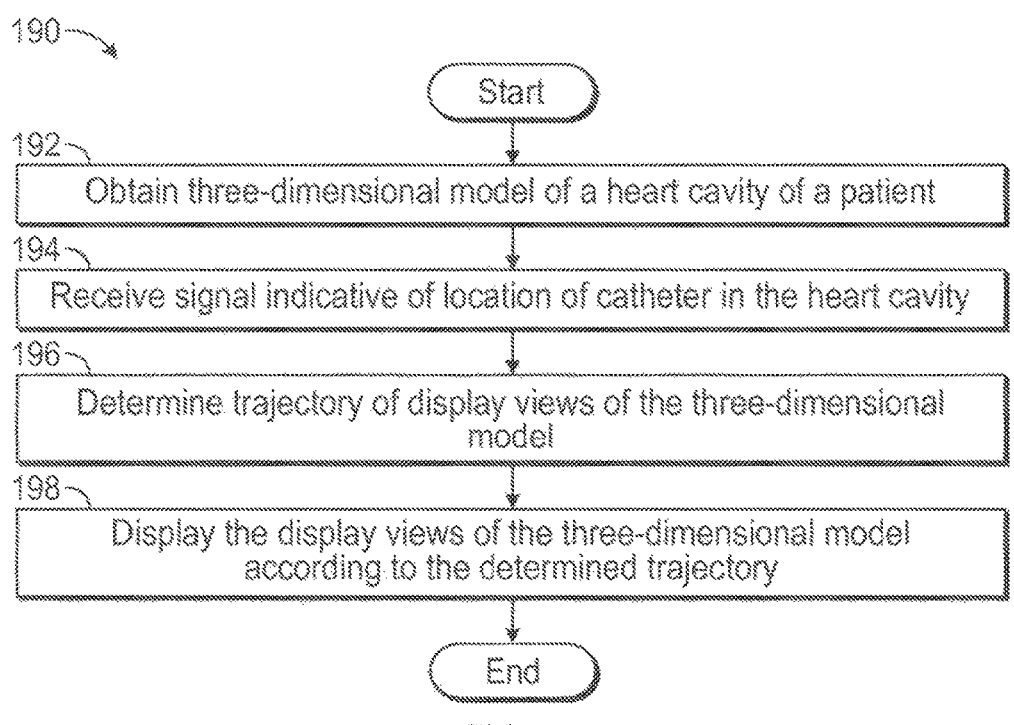
FIG. 9 is a flow chart of an exemplary process of displaying the three-dimensional model of FIG. 4 onto the graphical user interface of FIG. 1.

Referring now to FIG. 9, an exemplary method 190 of displaying a three-dimensional representation of a patient's heart cavity can include obtaining 192 a three-dimensional model of the heart cavity of the patient, receiving 194 a signal indicative of location of a catheter in the heart cavity of the patient, determining 196 a trajectory of display views of the three-dimensional model of the heart cavity, and displaying 198 display views of the three-dimensional model of the heart cavity on a graphical user interface, according to the determined trajectory. Determining 196 the trajectory of the display views of the three-dimensional model can be based at least in part on the received 194 location of the catheter and on one or more previously received locations of the catheter in the heart cavity. It should be appreciated that, although described below in the context of a heart cavity, the exemplary method 190 can be carried out to display a three-dimensional model of other anatomic structures of a patient such as, for example, the brain, the lungs, the sinuses, and/or other hollow anatomic structures of the patient through which a catheter may be passed for the purpose of diagnosis and/or treatment.

Obtaining 192 the three-dimensional model of the heart cavity of the patient can include any one or more methods of obtaining a three-dimensional model described herein. Thus, for example, obtaining 192 the three-dimensional model can include receiving a plurality of locations of a catheter within the heart cavity and mapping the received locations according to any one or more of the methods described herein. In addition, or in the alternative, obtaining 192 the three-dimensional model of the heart cavity can include receiving one or more datasets of the heart cavity, optionally segmenting them to form a surface mesh, and registering the datasets to a coordinate system according to any one or more of the methods described herein.

Receiving 194 the signal indicative of the location of the catheter in the heart cavity of the patient can include any one or more of the methods of receiving such a signal described herein. Accordingly, the received 194 signal can include a signal based on a magnetic position sensor (e.g., magnetic position sensor 130 described above). Further, or in the alternative, the received 194 signal can include or be derived from a time-varying signal such as, for example, a signal from a magnetic position sensor.

Determining 196 the trajectory of the display views can, in general, be based on the received 194 location of the catheter and on one or more previously received locations of the catheter in the heart cavity. For example, determining 196 the trajectory of the display views can be based on a time-varying received 194 signal over a period of time. An example of determining 196 the trajectory of the display views, therefore, can include processing (e.g., low-pass filtering) the time-varying signals and/or the display views based on the time-varying signal received 194 over a period of time.

Processing display views determined based on a time-varying signal received 194 over a period of time can result in a trajectory of the display views. In addition, or as an alternative, determining 196 the trajectory of the display views can be based one or more previously displayed views. Thus, as used herein, the trajectory of the display views should be understood to include trend information related to the display views such that the next display view can be determined based on the trend information. For at least this reason, a person of ordinary skill in the art will understand that, as compared to display views based on an unprocessed signal indicative of catheter location, the determined 196 trajectory of the display views can be used as the basis of a more stabilized display of the three-dimensional model. As used herein, a stabilized display of the three-dimensional model is one that, as compared to an unstabilized display or less stabilized display, exhibits fewer and less rapid changes and therefore appears less shaky.

In certain implementations, determining 196 the trajectory of display views can be based on an analyzed shape of the three-dimensional model. For example, the analysis of the three-dimensional model can include analyzing a portion of the three-dimensional model local to the received 194 signal indicative of the current location of the catheter. This local analysis of the three-dimensional model can, in some instances, include analyzing a local feature of the three-dimensional model. In addition, or in the alternative, the analysis of the three-dimensional model can include analyzing one or more global features of the three-dimensional model. It should be appreciated that the analysis based on local and/or global features of the three-dimensional model can include any one or more of the analyses based on local and/or global features described herein.

In some implementations, determining 196 the trajectory of the display views can be based on one or more visualization preferences. Exemplary visualization preferences include any one or more of the visualization preferences described herein and, thus, may include a preferred orientation of the three-dimensional model.

Displaying 198 display views of the three-dimensional model of the heart cavity on a graphical user interface can be based on any one or more of the methods described herein. As an example, displaying 198 display views of the three-dimensional model of the heart cavity can include projecting the three-dimensional model onto a viewing plane defined in an image plane. It should be appreciated that the orientation of the three-dimensional model in this projection can be based on the determined 196 trajectory of display views.

Figure 10:
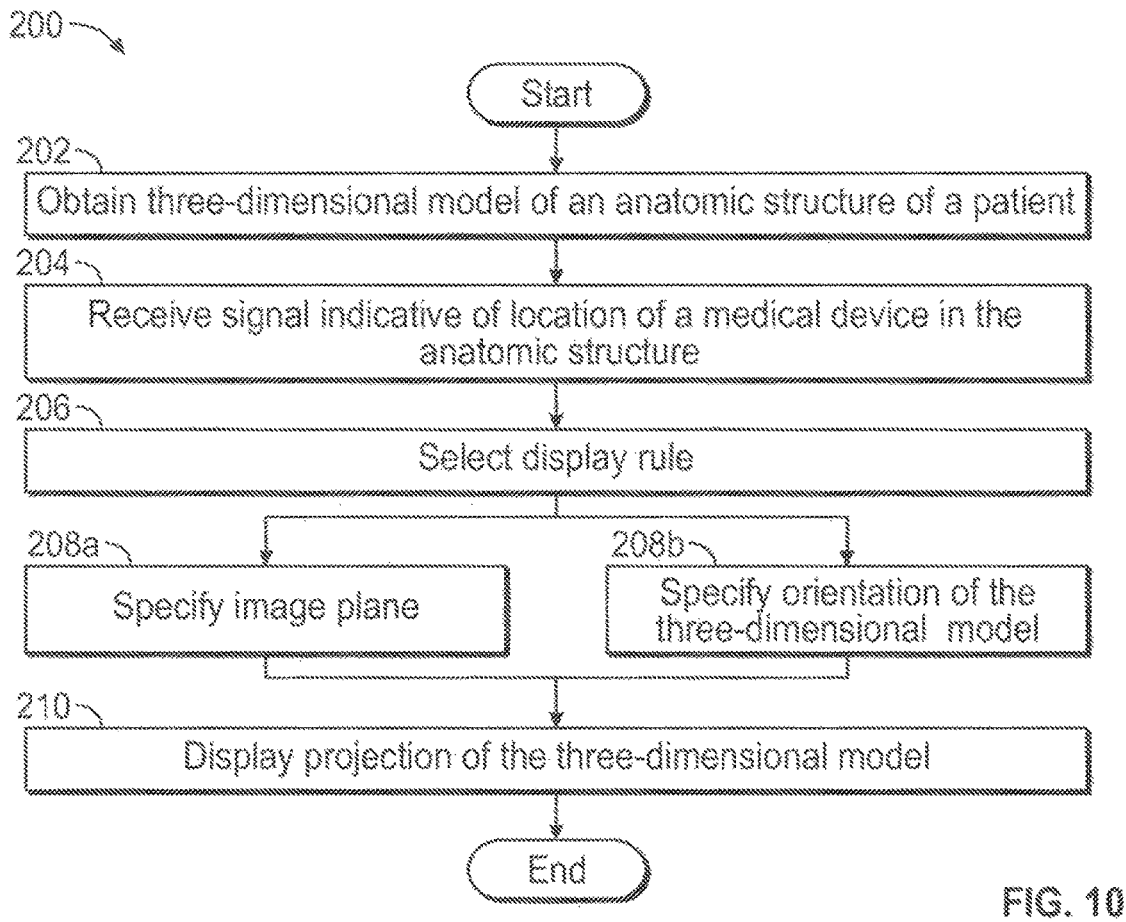
FIG. 10 is a flow chart of an exemplary process of displaying a three-dimensional model of an anatomic structure of a patient.

Referring now to FIG. 10, an exemplary method 200 of controlling a display of a three-dimensional model of an anatomic structure of a patient can include obtaining 202 the three-dimensional model of the anatomic structure of the patient, receiving 204 a signal indicative of a location of a medical device in the anatomic structure, selecting 206 a display rule, from a plurality of display rules, for specification of an orientation of the three-dimensional model and an image plane, specifying 208*a* the image plane, specifying 208*b* the orientation of the three-dimensional model, and displaying 210 at least a portion of a projection of the three-dimensional model (e.g., in the specified orientation and on the specified image plane) on a graphical user interface. Examples of the anatomic structure can include, without limitation, a heart cavity, the brain, the lungs, sinuses, and/or other hollow anatomic structures of the patient through which a catheter may be passed for the purpose of diagnosis and/or treatment. As described in greater detail below, specifying 208*a* the image plane and/or specifying 208*b* the orientation of the three-dimensional model can be based at least in part on the selected 206 display rule.

Obtaining 202 the three-dimensional model can include any one or more methods of obtaining a three-dimensional model described herein. As an example, obtaining 202 the three-dimensional model can include receiving a plurality of locations of a medical device (e.g., any one or more of the medical devices described herein) within the anatomic structure and mapping the received visited locations according to any one or more of the methods described herein. Further, or instead, obtaining 202 the three-dimensional model of the anatomic structure can include receiving one or more images of the anatomic structure and registering the images to a coordinate system according to any one or more of the methods described herein.

Receiving 204 the signal indicative of the location of the catheter in the anatomic structure of the patient can include any one or more of the methods of receiving such a signal described herein. Accordingly, the received 204 signal can include a signal based on a magnetic position sensor (e.g., magnetic position sensor 130 described above). In addition, or in the alternative, the received 204 signal can include a time-varying signal.

Selecting 206 a display rule, in general, can include selecting the display rule from the plurality of display rules. The plurality of display rules can include predetermined display rules and/or display rules based on inputs of a physician's preference. The selected 206 display rule can, as described in greater detail below, form a basis for the orientation of the three-dimensional model and the image plane for displaying 210 the projection of the three-dimensional model on the graphical user interface. Accordingly, it should be appreciated that any hierarchy of display rules described herein is provided by way of example, and not limitation, of achieving automated control of a display of the three-dimensional model of the anatomic structure during the medical procedure. Further, it should be appreciated that the selection 206 of the display rule from the plurality of display rules can, over the course of a medical procedure, reduce the amount of manual adjustment of the three-dimensional model required during the medical procedure, thus requiring less attention from the physician and improving efficiency of medical procedures.

Selecting 206 the display rule can be based at least in part on the received location of the medical device relative to the anatomic structure. In general, selecting 206 the display rule can include determining whether the applicable display rule is based on the received location of the medical device or based at least in part on the shape of the three-dimensional model. More specifically, a local display rule can be based at least in part on the received location of the medical device relative to the three-dimensional model, and a global display rule can be based at least in part on the shape of the three-dimensional model. In such instances, selecting 206 the display rule can include choosing the local display rule unless, based on the received location of the catheter, the local display rule is inappropriate, in which case the global display rule is chosen. The local display rule and the global display rule can be any one or more of the local display rules and the global display rules described herein.

Figure 11:
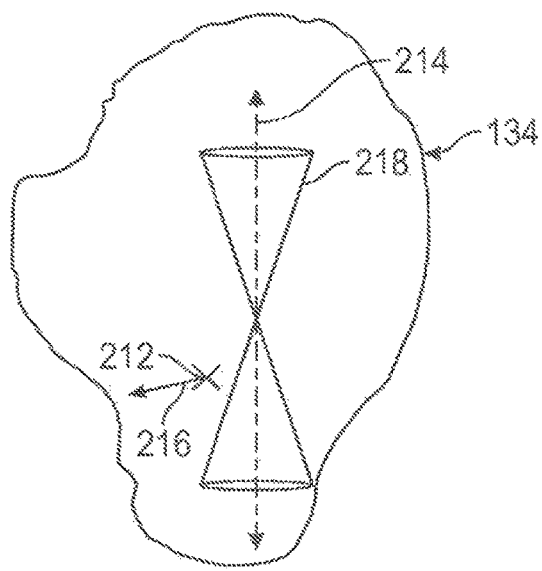
FIG. 11 is a schematic representation of a location of a tip section of the ablation catheter of FIG. 2, the location shown relative to the three-dimensional model of FIGS. 4 and 5.

Referring now to FIGS. 10 and 11, exemplary methods of selecting 206 the display rule are, for the sake of clarity, described with respect to a schematic representation of a location 212 of the tip section 124 of the catheter 104 relative to the three-dimensional model 134 of the heart cavity 132. It should be appreciated, however, that these exemplary methods of selecting 206 the display rule can be additionally, or alternatively, applicable to other types of medical devices, three-dimensional models, and/or anatomic structures.

A spatial reference 214 can be defined with respect to the three-dimensional model 134. In certain implementations, the spatial reference 214 can include a reference axis (e.g., as specified by a user). In such implementations, the spatial reference 214 can be aligned with a superior-inferior axis defined by the three-dimensional model. The spatial reference 214 aligned with a superior-inferior axis can facilitate, as an example, preferentially orienting the three-dimensional model 134 in a superior-inferior direction (e.g., with the projection of the three-dimensional model orienting in the "up" direction on the viewing window). This can be advantageous, in certain implementations, for displaying 210 the three-dimensional model 134 according to views consistent with other types of diagnostic imaging (e.g., x-ray).

Additionally, or alternatively, the spatial reference 214 can include a user input (e.g., received from one or more of a keyboard, a mouse, and a graphical user interface). By way of example and not limitation, the user input can include an indication of a predetermined preferred location and/or direction of the reference axis.

The location 212 of the tip section 124 of the catheter 104 can be based at least in part on the received 204 signal indicative of location of the tip section 124 of the catheter 104. A person of ordinary skill in the art will appreciate, therefore, that the selected 206 display rule can change as the location 212 of the tip section 124 changes during treatment. Such changes in the selection 206 of the display rule can facilitate automatically updating the display 210 of the projection of the three-dimensional model 134 to provide the physician with informative views of the three-dimensional model. Informative views of the three-dimensional model can include, by way of example and not limitation, views that are relatively unobscured, are in an expected orientation (e.g., consistent with an anatomic pose of the patient), and/or provide the physician with context with respect to the location 212 of the tip section 124 relative to the three-dimensional model 134.

A local direction vector 216 can be determined based on the received 204 signal indicative of the location of the catheter 204. In certain implementations, the local direction vector 216 can originate from the received 204 location of the catheter 104. Thus, in such implementations, the local direction vector 216 can point in a direction away from the catheter 204 and toward a surface of the three-dimensional model 134.

In general, selecting 206 the display rule can include comparing the location 212 of the catheter to a prohibited region 218 at least partially defined by the three-dimensional model. Based at least in part on this comparison, the local rule or the global rule can be selected. In instances in which the comparison results in a switching between the local rule and the global rule, the transition can be a gradual transition to facilitate a smooth transition of the display view on the graphical user interface. It should be appreciated that the prohibited region 218 represents a location 212 or a collection of locations 212 of the catheter in which selecting a local display rule can result in a view or a collection of views that have an increased likelihood of being unacceptable to the physician as being uninformative and/or disorienting. One example, among several, of such an uninformative and/or disorienting view corresponding to the prohibited region 218 is a view of the three-dimensional model 134 directly along the spatial reference 214 (e.g., along a superior-inferior axis).

The local direction vector 216 can be based at least in part on direction vectors normal to a surface of the three-dimensional model 134 in an area local to the received 204 location of the catheter 104. For example, the local direction vector 216 can be based at least in part on a surface normal direction determined according to any one or more of the methods described herein. Accordingly, the local direction vector 216 can be a weighted sum of direction vectors normal to a surface of the three-dimensional model 134 in an area local to the received 204 location of the catheter 104.

The prohibited region 218 can be at least partially defined by the three-dimensional model 134. For example, the prohibited region 218 can be at least partially defined by a center of mass of a volume of fluid represented by the three-dimensional model. As a more specific example, the prohibited region 218 can be substantially symmetric about at least one plane containing the center of mass. Additionally, or alternatively, the prohibited region 218 can be substantially symmetric about the spatial reference 214 (e.g., about a superior-inferior axis).

In certain implementations, the prohibited region 218 can include a double-infinite right cone. As used herein, the term "double-infinite right cone" includes two right circular cones (e.g., of the same size) placed apex to apex. The opening angle of each cone of the double-infinite right cone can be greater than about 5 degrees and less than about 90 degrees. The base of each cone of the double-infinite right cone can be, for example, perpendicular to a reference axis in implementations in which the spatial reference 214 includes the reference axis. In some implementations, the apices of the two right circular cones are at a center of mass of a volume of fluid represented by the three-dimensional model.

In implementations in which the prohibited region 218 includes a double-infinite right cone, comparing the location 212 of the catheter to the prohibited region 218 includes determining whether location 212 of the catheter is within either lobe of the double-infinite right cone. Continuing with this example, selecting 206 the display rule can include selecting the local rule or the global rule based on whether the location 212 of the catheter is within the double-infinite right cone. For example, the global rule can be selected 206 if the location 212 of the catheter is within a boundary of the prohibited region 218. Additionally, or alternatively, the local rule can be selected 206 if the location 212 of the catheter is a predetermined distance beyond a boundary of the prohibited region. This predetermined distance can be, for example, a transition region in which a combination of the local rule and the global rule is selected if the location 212 of the catheter is within the transition distance. Such a combination can be useful, for example, for producing smooth transitions resulting from moving the location 212 of the catheter into and out of the prohibited region 218. As an example, a relative weighting of the local rule to the global rule can be varied (e.g. substantially linearly) as a function of distance from the location 212 of the catheter to the prohibited region 218.

The prohibited region 218 including the double-infinite right cone can be advantageous, for example, for implementing a rule hierarchy based on symmetry in multiple directions. Additionally, or alternatively, the double-infinite right cone can be advantageous for displaying the three-dimensional model from the point of view of the catheter 104. While the prohibited region 218 is described as including a double-infinite right cone, it should be appreciated that other shapes of the prohibited region 218 are additionally, or alternatively, possible. For example, for certain anatomic structures, the prohibited region 218 can be appropriately shaped as a single cone, a cylinder, and/or a sphere.

If the local rule is selected 206 as the display rule, the specified 208a image plane can be perpendicular to the axis defined by the local direction vector 216. The image plane can be, for example, any one or more of the image planes described herein. Thus, the image plane can be a plane corresponding to a plane of a two-dimensional display of any one or more graphical user interfaces described herein. Additionally, or alternatively, if the local rule is selected 206, the pitch of the image plane relative to an axis (e.g., the spatial reference 214) can be limited by a predetermined amount. Further, or instead, if the local rule is selected 206, the roll of the viewing window can be limited by a predetermined amount relative to an axis (e.g., the spatial reference 214).

Continuing with implementations in which the local rule is the selected 206 display rule, the specified 208a image plane can be outside of a surface boundary of the three-dimensional model 134. Such a position of the image plane relative to the three-dimensional model 134 can be useful, for example, for providing context to the displayed 210 projection of the three-dimensional model. Such context can facilitate the physician's ability to identify anatomic features in the three-dimensional model 134 and, in some instances, facilitate positioning the catheter 104 in the heart cavity.

Continuing further with implementations in which the local rule is selected 206 as the display rule, the specified 208a image plane can be based in part on the direction of the local direction vector 216. More specifically, the specified 208a image plane can be perpendicular to the local direction vector 218. For example, the specified 208a image plane can be positioned relative to the local direction vector 216 such that the point of view of the displayed 210 projection of the three-dimensional model 134 is from the point of view of the tip section 124 of the catheter 104. Such a position of the specified 208a image plane relative to the local direction vector 216 can facilitate viewing the three-dimensional model 134 of the anatomic structure from the point of view of the tip section 124 of the catheter 104. It should be appreciated that such a point of view can be advantageous for providing an intuitive coordinate system for the physician to manipulate the tip section 124 of the catheter 104 within the anatomic structure.

If the local rule is selected 206 as the display rule, specifying 208*b* the orientation of the three-dimensional model 134 can include orienting a portion of the three-dimensional model 134 to extend in a predetermined preferred direction. As an example, in implementations in which the spatial reference 214 is a superior-inferior axis of the three-dimensional model 134, specifying 208*b* the orientation of the three-dimensional model 134 can include orienting a superior portion of the three-dimensional model 134 in the superior direction of the superior-inferior axis. This preferred orientation can be convenient for providing the physician with a familiar orientation of the anatomic structure represented in the three-dimensional model 134. Additionally, or alternatively, the portion of the three-dimensional model 134 and/or the predetermined preferred direction can be received as inputs through any one or more of the input devices described herein. It should be appreciated that, in use, these inputs can be useful for creating customized views of the anatomic structure represented by the three-dimensional model 134. Customization of this type can be useful, for example, for providing the physician with specific views that correspond to the physician's preferences and/or are necessitated by the particular medical procedure.

If the global rule is selected 206 as the display rule, specifying 208*a* the image plane and/or specifying 208*b* the orientation of the three-dimensional model 134 can include determining a thinnest direction of the three-dimensional model 134 of the anatomic structure. It should be appreciated that such a determination of the thinnest direction of the three-dimensional model 134 can include any one or more of the methods described herein. For example, the determination of the thinnest direction of the three-dimensional model 134 can be based on principal component analysis and/or a bounding box analysis.

Continuing with implementations in which the global rule is selected 206 as the display rule, specifying 208*a* the image plane can include specifying 208*a* the image plane in a plane perpendicular to an axis defined by the thinnest direction and/or an axis defined by the direction representing the least amount of mass in the three-dimensional model 134. Accordingly, in such implementations, the image plane can be parallel to the other directions of the coordinate system of the three-dimensional model 134. Because the thinnest direction and/or the direction representing the least amount of mass in the three-dimensional model is generally the direction that provides the physician with the least amount of context with respect to the three-dimensional model 134, specifying 208*a* the image plane parallel to one of the other directions in the coordinate system can be advantageous for providing the physician with context with respect to the three-dimensional model 134. Further, or in the alternative, the specified 208*a* image plane can be outside of a surface boundary of the three-dimensional model 134, which can be useful for providing additional or alternative context to the physician.

Continuing further with implementations in which the global rule is selected 206 as the display rule, specifying 208*b* the orientation of the three-dimensional model 134 can include orienting a portion of the three-dimensional model 134 in a preferred direction relative to the spatial reference 214. Such orientation can include any one or more methods described herein for orienting the three-dimensional model 134. Accordingly, it should be appreciated that the portion of the three-dimensional model 134 and/or the preferred direction can be predetermined (e.g., based on a received input according to any one or more of the input devices described herein).

Displaying 210 the projection of the three-dimensional model 134 on a graphical user interface can be carried out according to one or more of the methods described herein. For example, displaying 210 the projection of the three-dimensional model 134 can include determining a zoom magnitude. As another non-exclusive example, at least one dimension of the viewing window can be maintained at a fixed multiple of a dimension of the three-dimensional model 134 in the image plane.

In certain implementations, the zoom magnitude can be based at least in part on the determined displacement speed of the medical device according to any one or more of the methods described herein. In exemplary implementations, therefore, the zoom magnitude can increase as the displacement speed of the catheter 104 decreases.

Figure 12:
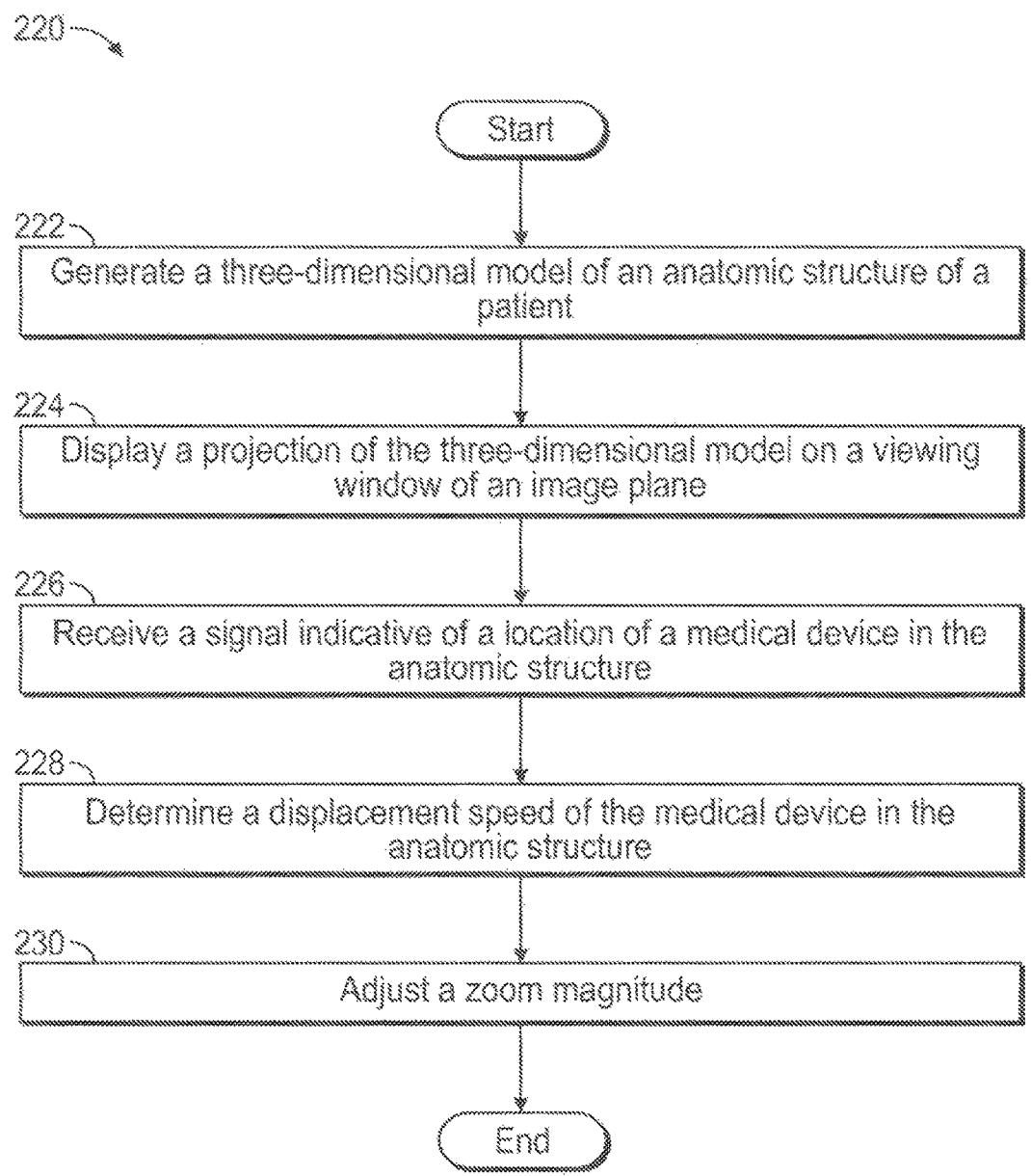
FIG. 12 is a flow chart of an exemplary process of controlling the size of a viewing window of the graphical user interface of FIG. 1.

Referring now to FIG. 12, an exemplary method 220 of controlling two-dimensional views of a three-dimensional anatomical model can include generating 222 a three-dimensional model of an anatomic structure of a patient, displaying 224 (e.g., on a graphical user interface) a projection of the three-dimensional model on a viewing window of an image plane, receiving 226 a signal indicative of a location of the medical device in the anatomic structure, determining 228 a displacement speed of the medical device in the anatomic structure, and adjusting 230 a zoom magnitude based at least in part on the determined displacement speed of the medical device. The exemplary method 220 can be carried out using any one or more of the devices and systems described herein and can be applicable to visualization of any of various, different medical devices during any of various, different medical procedures. Further, or instead, the anatomic structure of the patient can be any anatomic structure described herein, with examples including a heart cavity, the lungs, the brain, the sinuses, and/or any anatomic structure through which a catheter can be moved.

Generating 222 the three-dimensional model of the anatomic structure of the patient can include any one or more of the methods described herein. Thus, for example, generating 222 the three-dimensional model should be understood to include methods based on received locations of the medical device.

Displaying 224 the projection of the three-dimensional model on the viewing window of the image plane can include any one or more of the methods described herein. Similarly, receiving 226 the signal indicative of the location of the medical device can include any one or more of the methods described herein. Therefore, examples of displaying 224 the projection of the three-dimensional model and/or receiving 226 the signal indicative of the location of the medical device can include methods described with respect to FIGS. 4 and 5.

Determining 228 the displacement speed of the medical device in the anatomic structure can be based at least in part on the received 226 location of the medical device. Additionally, or alternatively, determining 228 the speed of the medical device can include any one or more of the methods described herein.

Adjusting 230 the zoom magnitude can include any of the methods described herein. As an example, adjusting 230 the zoom magnitude can include decreasing the size of the viewing window with decreasing displacement speed of the medical device. As an additional or alternative example, adjusting 230 the zoom magnitude can include adjusting a field of view. In certain implementations, the field of view can decrease as the displacement speed decreases. In some implementations, adjusting 230 the zoom magnitude can include adjusting a distance between the image plane and a center of projection. Additionally, or alternatively, adjusting 230 the zoom magnitude can include moving the viewing window and the center of projection (e.g., together) relative to the three-dimensional model. More generally, adjusting 230 the zoom magnitude can include any one or more adjustments that change the size of the projection of the three-dimensional model on the graphical user interface.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals.

It will further be appreciated that a realization of the processes or devices described above may include computer-executable code created using a structured programming language such as C, an object oriented programming language such as C++, or any other high-level or low level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices.

In another aspect, any of the systems and methods described above may be embodied in any suitable transmission or propagation medium carrying computer-executable code and/or any inputs or outputs from same.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

Thus, while particular embodiments have been shown and described, it will be apparent to those skilled in the art that various changes and modifications in form and details may be made therein without departing from the spirit and scope of this disclosure and are intended to form a part of the invention as defined by the following claims.

What is claimed is:

1. A method comprising:
   receiving a signal from a catheter, the signal indicative of a position of the catheter in a heart cavity of a patient;
   determining a geometric characteristic of a three-dimensional surface representation of the heart cavity, the three-dimensional surface representation constructed based, at least in part, on multiple positions visited by the catheter in the heart cavity; and
   determining a display view of the three-dimensional surface representation based, at least in part, on (i) the position of the catheter in the heart cavity, (ii) one or more previous positions of the catheter in the heart cavity, and (iii) the determined geometric characteristic of the three-dimensional surface representation,
   wherein determining the display view includes
   processing the received signal such that a transition from a previous display view to the determined display view is smooth and is perceived as continuous motion of the three-dimensional surface representation.

2. The method of claim 1 wherein determining the geometric characteristic includes calculating, in the three-dimensional surface representation, a surface-normal direction in an area of the heart cavity local to the position of the catheter.

3. The method of claim 2 wherein the surface-normal direction is a function of the position of the catheter and local characteristics of the three-dimensional surface representation local to the position of the catheter such that the display view automatically compensates for variations in angles of engagement between the catheter and target tissue.

4. The method of claim 1 wherein determining the geometric characterisitc includes determining a thinnest direction of the three-dimensional surface representation.

5. The method of claim 1 wherein determining the geometric characteristic is based on determining a bounding box with a smallest volume that contains the three-dimensional surface representation.

6. The method of claim 1, further comprising determining at least one visualization preference of the three-dimensional surface representation, wherein determining the display view is further based, at least in part, on the at least one visualization preference.

7. The method of claim 1 wherein determining the display view is based, at least in part, on the received signal over a period of time.

8. The method of claim 1 wherein determining the display view is further based, at least in part, on analysis of a shape of the three-dimensional surface representation.

9. The method of claim 1 wherein determining the display view is further based, at least in part, on visualization preferences.

10. The method of claim 1, further comprising transmitting, to a graphical user interface, the determined display view of the three-dimensional surface representation.

11. The method of claim 1, further comprising displaying, on a graphical user interface, the determined display view of the three-dimensional surface representation.

12. The method of claim 11 wherein determining the display view includes adjusting a size of the three-dimensional surface representation as projected onto a viewing window, and displaying the display view includes displaying a projection of the three-dimensional surface representation onto the graphical user interface according to the adjusted size.

13. A method comprising:
receiving, at a processing unit external to a patient, a signal from a catheter, the signal indicative of a position of the catheter in a heart cavity of the patient;
determining, at the processing unit, at least one geometric characteristic of a three-dimensional surface representation of the heart cavity, wherein the three-dimensional surface representation is constructed based, at least in part, on multiple positions visited by the catheter in the heart cavity, and wherein determining the at least one geometric characteristic includes calculating a surface-normal direction of the three-dimensional surface representation in an area of the three-dimensional surface representation closest to the position of the catheter;
determining, at the processing unit, a display view of the three-dimensional surface representation based at least in part on the position of the catheter in the heart cavity, on one or more previous positions of the catheter in the heart cavity, and on the geometric characteristic of the three-dimensional surface representation; and
transmitting, from the processing unit to a graphical user interface, the display view of the three-dimensional surface representation.

14. The method of claim 13 wherein the surface-normal direction is a function of the position of the catheter and local characteristics of the three-dimensional surface representation local to the position of the catheter such that the display view automatically compensates for variations in angles of engagement between the catheter and target tissue.

15. The method of claim 13 wherein determining the at least one geometric characterisitc further includes determining a thinnest direction of the three-dimensional surface representation.

16. The method of claim 13, further comprising determining at least one visualization preference of the three-dimensional surface representation, wherein determining the display view is further based, at least in part, on the at least one visualization preference.

17. The method of claim 13 wherein determining the display view of the three-dimensional surface representation is based, at least in part, on the received signal over a period of time and/or on one or more previous display views.

18. The method of claim 13 wherein determining the display view is further based, at least in part, on analysis of a shape of the three-dimensional surface representation.

19. The method of claim 13 wherein determining the display view is further based, at least in part, on visualization preferences.

20. The method of claim 13 wherein determining the display view includes adjusting a size of the three-dimensional surface representation as projected onto a viewing window, and displaying the display view includes displaying a projection of the three-dimensional surface representation onto the graphical user interface according to the adjusted size.

21. A method of treating a patient, the method comprising:
receiving a signal from a catheter, wherein the signal is indicative of a position of the catheter in a heart cavity of the patient;
determining a geometric characteristic of a three-dimensional surface representation of the heart cavity; and
determining a display view of the three-dimensional surface representation based, at least in part, on (i) the position of the catheter in the heart cavity, (ii) one or more previous positions of the catheter in the heart cavity, and (iii) the determined geometric characteristic of the three-dimensional surface representation,
wherein determining the display view includes processing the received signal such that a transition from a previous display view to the determined display view is smooth and is perceived as continuous motion of the three-dimensional surface representation.

22. The method of claim 21 wherein determining the geometric characteristic includes calculating a surface-normal direction of the three-dimensional surface representation in an area of the heart cavity closest to the position of the catheter.

23. The method of claim 21 wherein determining the display view further comprises processing the display view such that the determined display view is based on one or more previous display views.

24. The method of claim 21 wherein determining the display view is further based, at least in part, on:
the received signal over a period of time;
analysis of a shape of the three-dimensional surface representation;
at least one visualization preference; and/or
variations in angles of engagement between the catheter and target tissue.

25. The method of claim 21, further comprising:
transmitting the determined display view of the three-dimensional surface representation to a graphical user interface; and/or
displaying the determined display view of the three-dimensional surface representation on the graphical user interface.

* * * * *

UNITED STATES PATENT AND TRADEMARK OFFICE
CERTIFICATE OF CORRECTION

PATENT NO. : 10,467,801 B2
APPLICATION NO. : 16/188806
DATED : November 5, 2019
INVENTOR(S) : Doron Harlev et al.

Page 1 of 1

It is certified that error appears in the above-identified patent and that said Letters Patent is hereby corrected as shown below:

In the Specification

In Column 13, Line 21, delete "(MM)" and insert -- (MRI) --, therefor.

In the Claims

In Column 30, Line 66, in Claim 4, delete "characterisitc" and insert -- characteristic --, therefor.

In Column 31, Line 63, in Claim 15, delete "characterisitc" and insert -- characteristic --, therefor.

Signed and Sealed this
Second Day of June, 2020

Andrei Iancu
*Director of the United States Patent and Trademark Office*